United States Patent
Flaherty

(10) Patent No.: US 6,656,159 B2
(45) Date of Patent: Dec. 2, 2003

(54) DISPENSER FOR PATIENT INFUSION DEVICE

(75) Inventor: J. Christopher Flaherty, Topsfield, MA (US)

(73) Assignee: Insulet Corporation, Beverly, MA (US)

( * ) Notice: Subject to any disclaimer, the term of this patent is extended or adjusted under 35 U.S.C. 154(b) by 0 days.

(21) Appl. No.: 10/128,205

(22) Filed: Apr. 23, 2002

(65) Prior Publication Data

US 2003/0199825 A1 Oct. 23, 2003

(51) Int. Cl.$^7$ ............................................... A61M 37/00
(52) U.S. Cl. ........................................ 604/131; 604/151
(58) Field of Search ................................. 604/131, 132, 604/154, 151, 155, 134, 135, 153, 152, 133, 530, 531; 606/78, 105

(56) References Cited

U.S. PATENT DOCUMENTS

| | | |
|---|---|---|
| 3,631,847 A | 1/1972 | Hobbs |
| 3,812,843 A | 5/1974 | Wootten et al. |
| 4,067,000 A | 1/1978 | Carlson |
| 4,108,177 A | 8/1978 | Pistor |
| 4,151,845 A | 5/1979 | Clemens |
| 4,211,998 A | 7/1980 | Junginger et al. |
| 4,231,019 A | 10/1980 | Junginger et al. |
| 4,268,150 A | 5/1981 | Chen |
| 4,364,385 A | 12/1982 | Lossef |
| 4,373,527 A | 2/1983 | Fischell |
| 4,424,720 A | 1/1984 | Bucchianeri |
| 4,435,173 A | 3/1984 | Siposs et al. |
| 4,469,481 A | 9/1984 | Kobayashi |
| 4,475,901 A | 10/1984 | Kraegen et al. |
| 4,498,843 A | 2/1985 | Schneider et al. |
| 4,507,115 A * | 3/1985 | Kambara et al. ............ 604/135 |
| 4,514,732 A | 4/1985 | Hayes, Jr. |

(List continued on next page.)

FOREIGN PATENT DOCUMENTS

| | | |
|---|---|---|
| DE | 4200595 | 7/1993 |
| DE | 19920896 | 9/2000 |
| EP | 0342947 | 5/1989 |
| EP | 0763369 | 3/1997 |
| EP | 0867196 | 3/1998 |
| EP | 0937475 | 8/1999 |
| WO | WO81/01658 | 6/1981 |
| WO | WO86/06796 | 11/1986 |

(List continued on next page.)

OTHER PUBLICATIONS

US 5,954,699, 9/1999, Jost et al. (withdrawn)
Web–Site Brochure dated Jan. 4, 2000. MiniMed 508. "Doing its job. Naturally." www.minimed.com/tiles/mm$_{13}$ 113.htm.
Web–Site Brochure dated Dec. 20, 1999. Applied Medical Technology. "508 Pump Information". www.applied–medical.co.uk/508.htm.

(List continued on next page.)

Primary Examiner—Sharon Kennedy
(74) Attorney, Agent, or Firm—McDermott, Will & Emery

(57) ABSTRACT

A device for delivering fluid, such as insulin for example, to a patient. The device includes an exit port assembly, a syringe-like reservoir including a side wall extending towards an outlet connected to the exit port assembly. A threaded lead screw is received in the reservoir and a plunger has an outer periphery linearly slideable along the side wall of the reservoir and an inner periphery threadedly received on the lead screw. The plunger is non-rotatable with respect to the side wall such that rotating the lead screw causes the plunger to advance within the reservoir and force fluid through the outlet. The device also includes a dispenser having a return element for causes rotation of the lead screw, and a shape memory element. A changeable length of the shape memory element decreasing from an uncharged length to a charged length resets the return element.

129 Claims, 10 Drawing Sheets

U.S. PATENT DOCUMENTS

| | | |
|---|---|---|
| 4,529,401 A | 7/1985 | Leslie et al. |
| 4,559,033 A | 12/1985 | Stephen et al. |
| 4,559,037 A | 12/1985 | Franetzki et al. |
| 4,560,979 A | 12/1985 | Rosskopk |
| 4,562,751 A | 1/1986 | Nason et al. |
| 4,585,439 A | 4/1986 | Michel |
| 4,601,707 A | 7/1986 | Albisser et al. |
| 4,624,661 A | 11/1986 | Arimond |
| 4,634,427 A | 1/1987 | Hannula et al. |
| 4,678,408 A | 7/1987 | Nason et al. |
| 4,684,368 A | 8/1987 | Kenyon |
| 4,685,903 A | 8/1987 | Cable et al. |
| 4,734,092 A | 3/1988 | Millerd |
| 4,755,173 A | 7/1988 | Konopka et al. |
| 4,781,688 A | 11/1988 | Thoma et al. |
| 4,781,693 A | 11/1988 | Martinez et al. |
| 4,801,957 A | 1/1989 | Vandemoere |
| 4,808,161 A | 2/1989 | Kamen |
| 4,836,752 A | 6/1989 | Burkett |
| D303,013 S | 8/1989 | Konopka |
| 4,855,746 A | 8/1989 | Stacy |
| 4,882,600 A | 11/1989 | Van de Moere |
| 4,886,499 A | 12/1989 | Cirelli et al. |
| 4,898,579 A | 2/1990 | Konopka et al. |
| D306,691 S | 3/1990 | Arai |
| D311,735 S | 10/1990 | Aran et al. |
| 4,969,874 A | 11/1990 | Michel et al. |
| 4,973,998 A | 11/1990 | Gates |
| D315,727 S | 3/1991 | Arai et al. |
| 5,007,458 A | 4/1991 | Marcus et al. |
| 5,045,871 A | 9/1991 | Reinholdson |
| 5,062,841 A | 11/1991 | Siegel |
| 5,109,850 A | 5/1992 | Blanco et al. |
| 5,176,662 A | 1/1993 | Bartholomew et al. |
| 5,178,609 A * | 1/1993 | Ishikawa ............... 604/131 |
| 5,205,819 A | 4/1993 | Ross et al. |
| 5,213,483 A | 5/1993 | Flaherty et al. |
| 5,232,439 A | 8/1993 | Campbell et al. |
| 5,239,326 A | 8/1993 | Takai |
| 5,242,406 A | 9/1993 | Gross et al. |
| 5,244,463 A | 9/1993 | Cordner, Jr. et al. |
| 5,254,096 A | 10/1993 | Rondelet et al. |
| 5,257,980 A | 11/1993 | Van Antwerp et al. |
| 5,281,202 A | 1/1994 | Weber et al. |
| 5,312,337 A | 5/1994 | Flaherty et al. |
| 5,318,540 A | 6/1994 | Athayde et al. |
| 5,342,313 A | 8/1994 | Campbell et al. |
| 5,411,480 A | 5/1995 | Kriesel |
| 5,433,710 A | 7/1995 | Van Antwerp et al. |
| 5,452,033 A | 9/1995 | Balling et al. |
| 5,492,534 A | 2/1996 | Athayde et al. |
| 5,505,709 A | 4/1996 | Funderburk et al. |
| 5,507,288 A | 4/1996 | Bocker et al. ............... 128/633 |
| 5,514,096 A | 5/1996 | Hiejima |
| 5,533,389 A | 7/1996 | Kamen et al. |
| 5,545,152 A | 8/1996 | Funderburk et al. |
| 5,575,770 A | 11/1996 | Melsky et al. |
| 5,576,781 A | 11/1996 | Deleeuw |
| 5,582,593 A | 12/1996 | Hultman |
| 5,584,813 A | 12/1996 | Livingston et al. |
| 5,630,710 A | 5/1997 | Tune et al. |
| 5,637,095 A | 6/1997 | Nason et al. |
| 5,643,213 A | 7/1997 | McPhee |
| 5,647,853 A | 7/1997 | Feldmann et al. |
| 5,660,728 A | 8/1997 | Saaski et al. |
| 5,665,065 A | 9/1997 | Colman et al. |
| 5,665,070 A | 9/1997 | McPhee |
| 5,695,490 A | 12/1997 | Flaherty et al. |
| 5,702,363 A | 12/1997 | Flaherty |
| 5,704,520 A | 1/1998 | Gross |
| 5,726,404 A | 3/1998 | Brody |
| 5,726,751 A | 3/1998 | Altendorf et al. |
| 5,741,228 A | 4/1998 | Lambrecht et al. |
| 5,747,350 A | 5/1998 | Sattler |
| 5,748,827 A | 5/1998 | Holl et al. |
| 5,755,682 A | 5/1998 | Knudson et al. |
| 5,776,103 A | 7/1998 | Kriesel et al. |
| 5,779,676 A | 7/1998 | Kriesel et al. |
| 5,785,681 A | 7/1998 | Indravudh |
| 5,785,688 A | 7/1998 | Joshi et al. |
| 5,797,881 A | 8/1998 | Gadot |
| 5,800,397 A | 9/1998 | Wilson et al. |
| 5,800,405 A | 9/1998 | McPhee |
| 5,810,015 A | 9/1998 | Flaherty |
| 5,814,020 A | 9/1998 | Gross |
| 5,839,467 A | 11/1998 | Saaski et al. |
| 5,840,063 A | 11/1998 | Flaherty |
| 5,845,218 A | 12/1998 | Altschul |
| 5,848,991 A | 12/1998 | Gross et al. |
| 5,851,197 A | 12/1998 | Marano et al. |
| 5,858,005 A | 1/1999 | Kriesel |
| D405,524 S | 2/1999 | Falk et al. |
| 5,875,393 A | 2/1999 | Altschul et al. |
| 5,886,647 A | 3/1999 | Badger et al. |
| 5,891,097 A | 4/1999 | Saito et al. |
| 5,897,530 A | 4/1999 | Jackson |
| 5,906,597 A | 5/1999 | McPhee |
| 5,911,716 A | 6/1999 | Rake et al. |
| 5,919,167 A | 7/1999 | Mulhauser et al. |
| 5,931,814 A | 8/1999 | Alex et al. |
| 5,935,099 A | 8/1999 | Peterson et al. |
| 5,954,058 A | 9/1999 | Flaherty |
| 5,957,890 A | 9/1999 | Mann et al. |
| 5,965,848 A | 10/1999 | Altschul et al. |
| 5,983,094 A | 11/1999 | Altschul et al. |
| 5,993,423 A | 11/1999 | Choi |
| 5,997,501 A | 12/1999 | Gross et al. |
| 6,019,747 A | 2/2000 | McPhee |
| 6,061,580 A | 5/2000 | Altschul et al. |
| 6,071,292 A | 6/2000 | Makower et al. |
| 6,144,847 A | 11/2000 | Altschul et al. |
| 6,152,898 A | 11/2000 | Olsen |
| 6,190,359 B1 * | 2/2001 | Heruth ............... 604/131 |
| 6,375,638 B2 * | 4/2002 | Nason et al. ............... 604/132 |
| 6,488,652 B1 * | 12/2002 | Weijand et al. ............... 604/93.01 |

FOREIGN PATENT DOCUMENTS

| | | |
|---|---|---|
| WO | WO98/00193 | 1/1998 |
| WO | WO98/01071 | 1/1998 |
| WO | WO00/19887 | 9/1999 |
| WO | WO99/62576 | 9/1999 |
| WO | WO99/56803 | 11/1999 |
| WO | WO0010628 | 3/2000 |
| WO | WO00/29047 | 5/2000 |
| WO | WO00/29049 | 5/2000 |
| WO | WO00/74752 | 5/2000 |
| WO | WO00/30705 | 6/2000 |
| WO | WO00/78210 | 6/2000 |
| WO | WO00/48112 | 8/2000 |
| WO | WO00/61215 | 10/2000 |
| WO | WO01/52727 | 1/2001 |
| WO | WO01/5663 | 8/2001 |
| WO | WO01/76684 | 10/2001 |
| WO | WO 02/20073 | 3/2002 |

OTHER PUBLICATIONS

Web–Site Brochure dated Jan. 1, 2000. "The Glucose Sensor". www.animascorp.com/sensor_f.html.

Web–Site Brochure dated Dec. 20, 1999. "The Animas R–1000 Insulin Pump". www.animascorp.com/pump_f_s.html.

Web–Site Brochure dated Dec. 20, 1999. "The Animas R–1000 Insulin Pump". www.animascorp.com/pump_f_f.html.

Web–Site Brochure dated Jan. 4, 2000. SOOIL–Homepage. "Portable Insulin Pump". www.sooil.com/intro2.htm.

Web–Site Brochure dated Jan. 4, 2000. SOOIL–Homepage. "Portable Insulin Pump". www.sooil.com/prodcut2.htm.

Web–Site Brochure dated Jan. 4, 2000. SOOIL–Homepage. "Portable Insulin Pump". www.sooil.com/product3.htm.

Web–Site Brochure dated Jan. 4, 2000. SOOIL–Homepage. "Portable Insulin Pump". www.sooil.com/product4.htm.

* cited by examiner

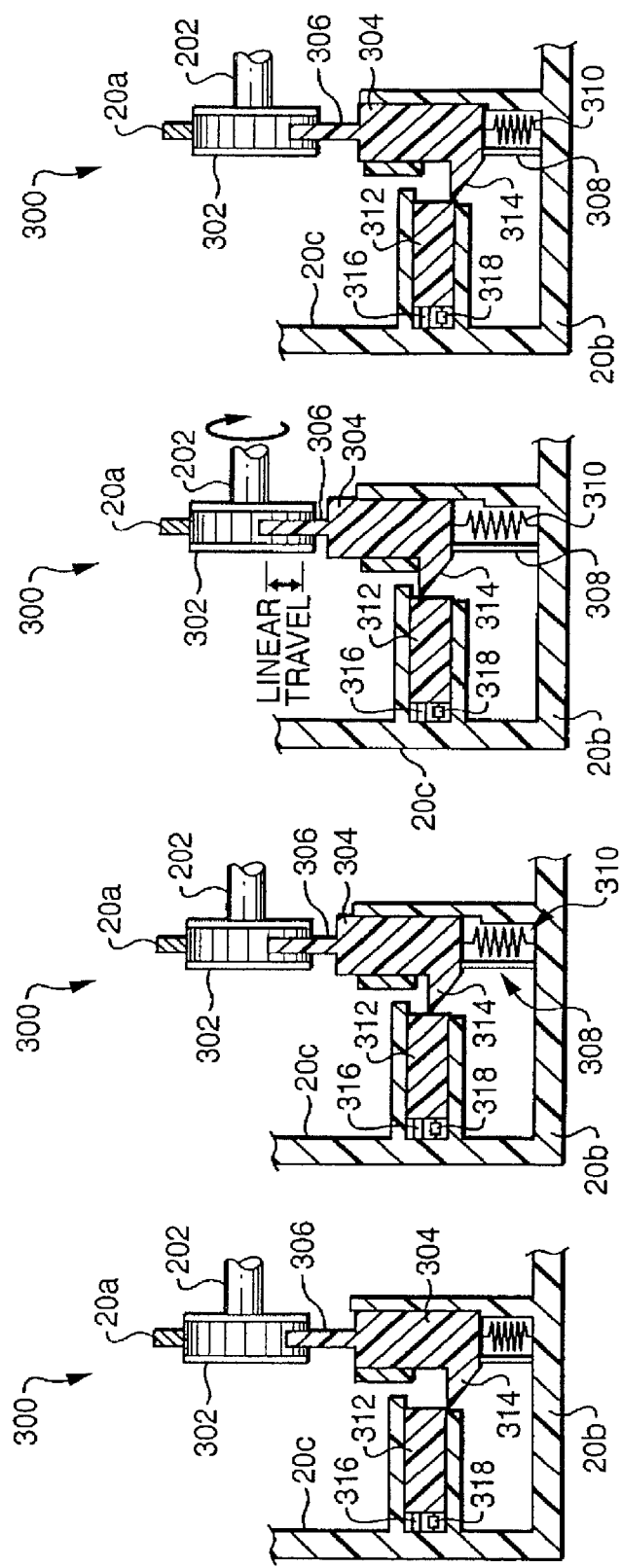

DISPENSER FOR PATIENT INFUSION DEVICE

CROSS-REFERENCE TO RELATED APPLICATIONS

The present application is related to co-pending U.S. patent application Ser. No. 10/128,203 which was filed on the same day as the present application, is entitled DISPENSER FOR PATIENT INFUSION DEVICE, and is assigned to the assignee of the present application and incorporated herein by reference.

The present application is related to co-pending U.S. patent application Ser. No. 09/943,992, filed on Aug. 31, 2001 and entitled DEVICES, SYSTEMS AND METHODS FOR PATIENT INFUSION, which is assigned to the assignee of the present application and incorporated herein by reference.

FIELD OF THE INVENTION

The present invention relates generally to medical devices, systems and methods, and more particularly to small, low cost, portable infusion devices and methods that are useable to achieve precise, sophisticated, and programmable flow patterns for the delivery of therapeutic liquids such as insulin to a mammalian patient. Even more particularly, the present invention is directed to a dispenser for a fluid delivery device that utilizes a shape memory element.

BACKGROUND OF THE INVENTION

Today, there are numerous diseases and other physical ailments that are treated by various medicines including pharmaceuticals, nutritional formulas, biologically derived or active agents, hormonal and gene based material and other substances in both solid or liquid form. In the delivery of these medicines, it is often desirable to bypass the digestive system of a mammalian patient to avoid degradation of the active ingredients caused by the catalytic enzymes in the digestive tract and liver. Delivery of a medicine other than by way of the intestines is known as parenteral delivery. Parenteral delivery of various drugs in liquid form is often desired to enhance the effect of the substance being delivered, insuring that the unaltered medicine reaches its intended site at a significant concentration. Also, undesired side effects associated with other routes of delivery, such as systemic toxicity, can potentially be avoided.

Often, a medicine may only be available in a liquid form, or the liquid version may have desirable characteristics that cannot be achieved with solid or pill form. Delivery of liquid medicines may best be accomplished by infusing directly into the cardiovascular system via veins or arteries, into the subcutaneous tissue or directly into organs, tumors, cavities, bones or other site specific locations within the body.

Parenteral delivery of liquid medicines into the body is often accomplished by administering bolus injections using a needle and reservoir, or continuously by gravity driven dispensers or transdermal patch technologies. Bolus injections often imperfectly match the clinical needs of the patient, and usually require larger individual doses than are desired at the specific time they are given. Continuous delivery of medicine through gravity feed systems compromise the patient's mobility and lifestyle, and limit the therapy to simplistic flow rates and profiles. Transdermal patches have special requirements of the medicine being delivered, particularly as it relates to the molecular structure, and similar to gravity feed systems, the control of the drug administration is severely limited.

Ambulatory infusion pumps have been developed for delivering liquid medicaments to a patient. These infusion devices have the ability to offer sophisticated fluid delivery profiles accomplishing bolus requirements, continuous infusion and variable flow rate delivery. These infusion capabilities usually result in better efficacy of the drug and therapy and less toxicity to the patient's system. An example of a use of an ambulatory infusion pump is for the delivery of insulin for the treatment of diabetes mellitus. These pumps can deliver insulin on a continuous basal basis as well as a bolus basis as is disclosed in U.S. Pat. No. 4,498,843 to Schneider et al.

The ambulatory pumps often work with a reservoir to contain the liquid medicine, such as a cartridge, a syringe or an IV bag, and use electromechanical pumping or metering technology to deliver the medication to the patient via tubing from the infusion device to a needle that is inserted transcutaneously, or through the skin of the patient. The devices allow control and programming via electromechanical buttons or switches located on the housing of the device, and accessed by the patient or clinician. The devices include visual feedback via text or graphic screens, such as liquid crystal displays known as LCD's, and may include alert or warning lights and audio or vibration signals and alarms. The device can be worn in a harness or pocket or strapped to the body of the patient.

Currently available ambulatory infusion devices are expensive, difficult to program and prepare for infusion, and tend to be bulky, heavy and very fragile. Filling these devices can be difficult and require the patient to carry both the intended medication as well as filling accessories. The devices require specialized care, maintenance, and cleaning to assure proper functionality and safety for their intended long term use. Due to the high cost of existing devices, healthcare providers limit the patient populations approved to use the devices and therapies for which the devices can be used.

Clearly, therefore, there was a need for a programmable and adjustable infusion system that is precise and reliable and can offer clinicians and patients a small, low cost, light-weight, easy-to-use alternative for parenteral delivery of liquid medicines.

In response, the applicant of the present application provided a small, low cost, light-weight, easy-to-use device for delivering liquid medicines to a patient. The device, which is described in detail in co-pending U.S. application Ser. No. 09/943,992, filed on Aug. 31, 2001, includes an exit port, a dispenser for causing fluid from a reservoir to flow to the exit port, a local processor programmed to cause a flow of fluid to the exit port based on flow instructions from a separate, remote control device, and a wireless receiver connected to the local processor for receiving the flow instructions. To reduce the size, complexity and costs of the device, the device is provided with a housing that is free of user input components, such as a keypad, for providing flow instructions to the local processor.

What are still desired are new and improved components, such as dispensers and reservoirs, for a device for delivering fluid to a patient. Preferably, the components will be simple in design, and relatively compact, lightweight, easy to manufacture and inexpensive, such that the resulting fluid delivery device can be effective, yet inexpensive and disposable.

SUMMARY OF THE INVENTION

The present invention provides a device for delivering fluid, such as insulin for example, to a patient. The device includes an exit port assembly, a reservoir including a side wall extending towards an outlet connected to the exit port assembly, and a threaded lead screw received in the reservoir and extending towards the outlet of the reservoir. A plunger is secured to the lead screw and has an outer periphery linearly slideable along the side wall of the reservoir. The plunger and the lead screw are operatively arranged such that rotation of the lead screw in a first direction causes the plunger to slide along the side wall towards the outlet of the reservoir, which in turn causes fluid within the reservoir to be dispensed to the exit port assembly. The device also includes a dispenser having a shape memory element having a changeable length decreasing from an uncharged length to a charged length when at least one charge is applied to the shape memory element. The shape memory element has a first end secured to the lead screw, a portion of the elongated shape memory element wrapped around the lead screw, and a second end fixed with respect to the lead screw, such that the changeable length of the shape memory element decreasing from an uncharged length to a charged length causes rotation of the lead screw in the first direction. The use of a shape memory element helps provide a dispenser that is simple in design, and relatively compact, lightweight, and easy to manufacture.

The present invention provides another device for delivering fluid. The device includes an exit port assembly, a reservoir having a side wall extending towards an outlet connected to the exit port assembly, and a threaded lead screw received in the reservoir. A plunger is secured to the lead screw and has an outer periphery linearly slideable along the side wall of the reservoir. The plunger and the lead screw are operatively arranged such that rotation of the lead screw in a first direction causes the plunger to slide along the side wall towards the outlet of the reservoir. The device also includes a ratchet mechanism secured to the lead screw and including a wheel arranged such that rotation of the wheel in the first direction causes rotation of the lead screw in the first direction, while rotation of the wheel in a second direction causes no rotation of the lead screw. The device further includes a dispenser includes an elongated shape memory element having a changeable length decreasing from an uncharged length to a charged length when at least one charge is applied to the shape memory element. The shape memory element operatively connected to the wheel of the ratchet mechanism such that the changeable length of the shape memory element decreasing from an uncharged length to a charged length causes rotation of the wheel in one of the first direction and the second direction. An actuation element is secured to the wheel for moving the wheel in the other of the first direction and the second direction.

The present invention provides an additional device for delivering fluid. The device includes an exit port assembly, a reservoir including a side wall extending towards an outlet connected to the exit port assembly, and a threaded lead screw received in the reservoir. A plunger is secured to the lead screw and has an outer periphery linearly slideable along the side wall of the reservoir. The plunger and the lead screw are operatively arranged such that rotation of the lead screw in a first direction causes the plunger to slide along the side wall towards the outlet of the reservoir. A gear is secured to the lead screw and has radially extending teeth positioned to contact a first fixed member and prevent rotation of the gear and the lead screw in the second direction. The device also includes a dispenser having a slide positioned for linear movement adjacent the gear between a second fixed member and a third fixed member. The slide has a finger for engaging the teeth of the gear. The finger and the teeth are adapted such that linear movement of the slide past the gear towards the second fixed member causes rotation of the gear in the first direction, while linear movement of the slide past the gear towards the third fixed member causes no rotation of the gear. The dispenser further includes an elongated shape memory element having a changeable length decreasing from an uncharged length to a charged length when at least one charge is applied to the shape memory element. The shape memory element is connected between the slide and the third fixed member such that the changeable length of the shape memory element decreasing from an uncharged length to a charged length causes linear movement of the slide past the gear towards the third fixed member. An actuation element is connected between the slide and the second fixed member for causing linear movement of the slide past the gear towards the second fixed member when the charge applied to the shape memory element is removed.

The present invention provides a further device for delivering fluid. The device includes an exit port assembly, a reservoir including a side wall extending towards an outlet connected to the exit port assembly, and a threaded lead screw received in the reservoir. A plunger is secured to the lead screw and has an outer periphery linearly slideable along the side wall of the reservoir. The plunger and the lead screw are operatively arranged such that rotation of the lead screw in a first direction causes the plunger to slide along the side wall towards the outlet of the reservoir. A gear is secured to the lead screw and includes radially extending teeth positioned to contact a first fixed member and prevent rotation of the gear and the lead screw in the second direction. The device also includes a dispenser having a slide positioned for linear movement between the gear and a second fixed member, the slide including a finger for engaging the teeth of the gear. The finger and the teeth are adapted such that linear movement of the slide towards the gear causes rotation of the gear in the first direction while linear movement of the slide towards the second fixed member causes no rotation of the gear. The dispenser further includes an elongated shape memory element having a changeable length decreasing from an uncharged length to a charged length when at least one charge is applied to the shape memory element, the shape memory element connected between the slide and the second fixed member such that the changeable length of the shape memory element decreasing from an uncharged length to a charged length causes linear movement of the slide towards the second fixed member. An actuation element is connected between the slide and the second fixed member for causing linear movement of the slide towards the gear.

The present invention, therefore, provides a device for delivering fluid to a patient including new and improved components, such as dispensers and reservoirs. The components are simple in design, and relatively compact, lightweight, easy to manufacture and inexpensive, such that the resulting fluid delivery device is also relatively compact, lightweight, easy to manufacture and inexpensive such that the device can be inexpensive and disposable. In particular, the new and improved components of the present invention advantageously use shape memory elements to reduce complexity and costs.

The invention also provides an auxiliary component for use with the shape memory elements of the dispensers disclosed herein. An exemplary embodiment of the auxiliary component is provided in the form of an exit port assembly including a fixed member defining a channel having an outlet, and a transcutaneous patient access tool received for sliding movement in the channel towards the outlet. An actuation element is connected between the tool and a second fixed member for causing sliding movement of the tool towards the outlet of the channel, and a movable latch is positioned within the channel between the tool and the outlet. The exit port assembly also includes an elongated shape memory element connected to the latch such that the changeable length of the shape memory element decreasing from an uncharged length to a charged length causes movement of the latch out of the channel. The elongated shaped memory element can comprise one of the elongated shaped memory elements of the dispensers disclosed herein, such that a single elongated shaped memory element is used to operate two components.

The present invention provides still another device for delivering fluid. The device includes an exit port assembly, a fill port, and a reservoir including a side wall extending towards an outlet connected to the exit port assembly and an inlet connected to the fill port. A threaded lead screw is received in the reservoir and extends towards the outlet, and a plunger has an outer periphery slidably received on the side wall of the reservoir and an inner periphery slidably received on the lead screw. The plunger is non-rotatable with respect to the side wall and includes an insert having a threaded surface mateable with the threaded lead screw, and a spring biasing the threaded surface of the insert against the threaded lead screw such that rotating the lead screw in a first direction causes the plunger to slide along the side wall towards the outlet of the reservoir. The plunger also includes an elongated shape memory element having a first end secured to the insert and a second end extending radially outwardly from the insert and secured to the plunger, such that the changeable length of the shape memory element decreasing from an uncharged length to a charged length pulls the threaded surface of the insert away from the threaded lead screw. Applying a charge to the shape memory element, therefore, disengages the insert and allows the plunger to slide along the lead screw and away from the inlet of the reservoir during filling of the reservoir.

The present invention provides yet another device for delivering fluid. The device includes an exit port assembly, a fill port, a reservoir including a side wall extending towards an outlet connected to the exit port assembly and an inlet connected to the fill port, and a threaded lead screw received at least partly within the reservoir. A linearly fixed, annular gear is coaxially positioned on the threaded lead screw adjacent the reservoir and includes an insert having a threaded surface mateable with the threaded lead screw, a spring biasing the threaded surface of the insert against the threaded lead screw such that rotating the gear in a first direction causes the lead screw to move linearly towards the outlet of the reservoir, and an elongated shape memory element having a first end secured to the insert and a second end extending radially outwardly from the insert and secured to the gear. A changeable length of the shape memory element decreasing from an uncharged length to a charged length pulls the threaded surface of the insert away from the threaded lead screw such that the lead screw is movable linearly through the gear and away from the inlet of the reservoir. A plunger is secured to the lead screw and has an outer periphery linearly slideable along the side wall of the reservoir. During filling of the reservoir, the shape memory element can be charged to allow the plunger and lead screw to moved away from the fill port and the inlet of the reservoir.

These aspects of the invention together with additional features and advantages thereof may best be understood by reference to the following detailed descriptions and examples taken in connection with the accompanying illustrated drawings.

BRIEF DESCRIPTION OF THE DRAWINGS

FIGS. 16 through 19 are side elevation views, partially in section, illustrating operation of still another exemplary embodiment of a dispenser constructed in accordance with the present invention for turning the lead screw of the fluid delivery device of FIG. 1.

DETAILED DESCRIPTION OF EXEMPLARY EMBODIMENTS

Figure 2:
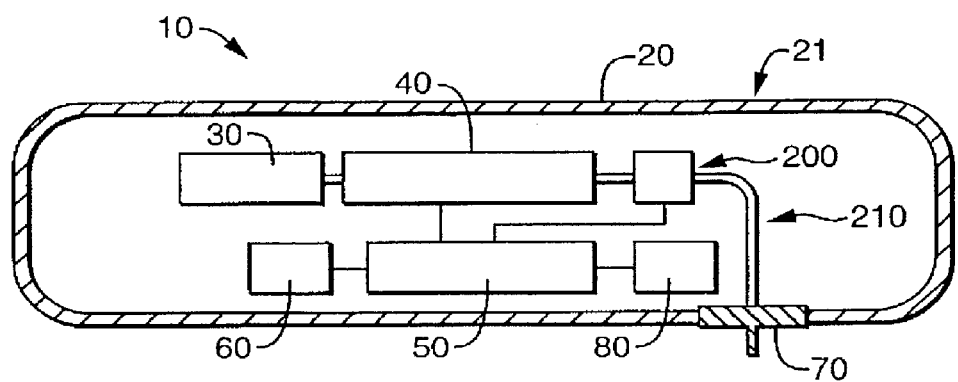
FIG. 2 is a sectional side view of the fluid delivery device of FIG. 1.

Referring first to FIG. 2, there is illustrated an exemplary embodiment of a fluid delivery device 10 including a dispenser 40 constructed in accordance with the present invention. The dispenser 40 causes fluid flow between a reservoir 30 and an exit port assembly 70 during operation of the device 10. In general, shape memory elements are utilized in accordance with the present invention to provide effective, yet simple and inexpensive dispensers for fluid delivery devices.

The fluid delivery device 10 of FIG. 2 can be used for the delivery of fluids to a person or animal. The types of liquids that can be delivered by the fluid delivery device 10 include, but are not limited to, insulin, antibiotics, nutritional fluids, total parenteral nutrition or TPN, analgesics, morphine, hormones or hormonal drugs, gene therapy drugs, anticoagulants, analgesics, cardiovascular medications, AZT or chemotherapeutics. The types of medical conditions that the fluid delivery device 10 might be used to treat include, but are not limited to, diabetes, cardiovascular disease, pain, chronic pain, cancer, AIDS, neurological diseases, Alzheimer's Disease, ALS, Hepatitis, Parkinson's Disease or spasticity. In addition, it should be understood that the dispenser 40 according to the present invention can be used with fluid delivery devices other than those used for the delivery of fluids to persons or animals.

Figure 1:
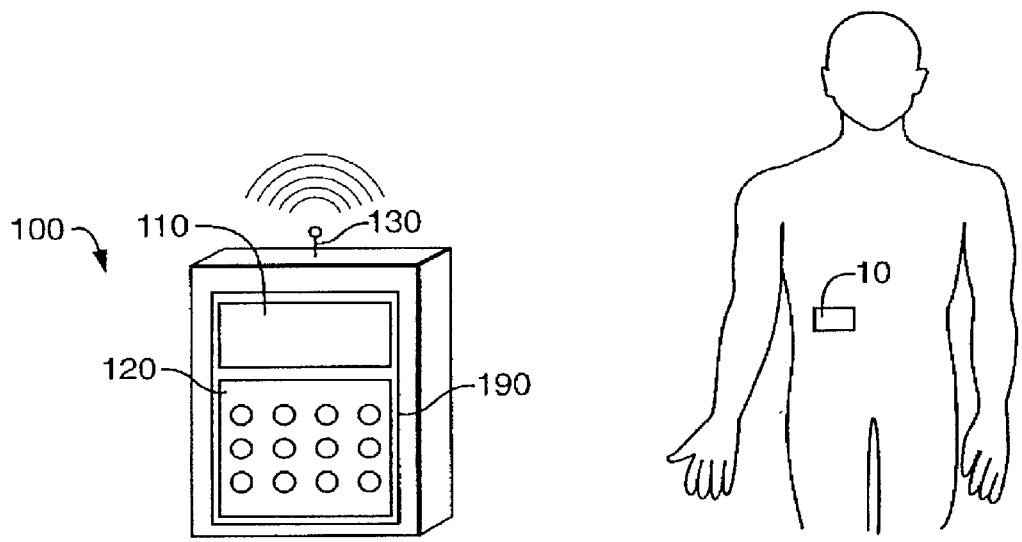
FIG. 1 is a perspective view of a first exemplary embodiment of a fluid delivery device constructed in accordance with the present invention and shown secured on a patient, and a remote control device for use with the fluid delivery device (the remote control device being enlarged with respect to the patient and the fluid delivery device for purposes of illustration)

The fluid delivery device 10 also includes a processor or electronic microcontroller (hereinafter referred to as the "local" processor) 50 connected to the dispenser 40. The local processor 50 is programmed to cause a flow of fluid to the exit port assembly 70 based on flow instructions from a separate, remote control device 100, an example of which is shown in FIG. 1. Referring also to FIG. 2, the fluid delivery device 10 further includes a wireless receiver 60 connected to the local processor 50 for receiving the flow instructions from the separate, remote control device 100 and delivering the flow instructions to the local processor. The device 10 also includes a housing 20 containing the exit port assembly 70, the reservoir 30, the dispenser 40, the local processor 50 and the wireless receiver 60.

As shown, the housing 20 of the fluid delivery device 10 is free of user input components for providing flow instructions to the local processor 50, such as electromechanical switches or buttons on an outer surface 21 of the housing, or interfaces otherwise accessible to a user to adjust the programmed flow rate through the local processor 50. The lack of user input components allows the size, complexity and costs of the device 10 to be substantially reduced so that the device 10 lends itself to being small and disposable in nature. Examples of such devices are disclosed in co-pending U.S. patent application Ser. No. 09/943,992, filed on Aug. 31, 2001 and entitled DEVICES, SYSTEMS AND METHODS FOR PATIENT INFUSION, which is assigned to the assignee of the present application and has previously been incorporated herein by reference.

In order to program, adjust the programming of, or otherwise communicate user inputs to the local processor 50, the fluid delivery device 10 includes the wireless communication element, or receiver 60 for receiving the user inputs from the separate, remote control device 100 of FIG. 1. Signals can be sent via a communication element (not shown) of the remote control device 100, which can include or be connected to an antenna 130, shown in FIG. 1 as being external to the device 100.

The remote control device 100 has user input components, including an array of electromechanical switches, such as the membrane keypad 120 shown. The control device 100 also includes user output components, including a visual display, such as a liquid crystal display (LCD) 110. Alternatively, the control device can be provided with a touch screen for both user input and output. Although not shown in FIG. 1, the remote control device 100 has its own processor (hereinafter referred to as the "remote" processor) connected to the membrane keypad 120 and the LCD 110. The remote processor receives the user inputs from the membrane keypad 120 and provides "flow" instructions for transmission to the fluid delivery device 10, and provides information to the LCD 110. Since the remote control device 100 also includes a visual display 110, the fluid delivery device 10 can be void of an information screen, further reducing the size, complexity and costs of the device 10.

The communication element 60 of the device 10 preferably receives electronic communication from the remote control device 100 using radio frequency or other wireless communication standards and protocols. In a preferred embodiment, the communication element 60 is a two-way communication element, including a receiver and a transmitter, for allowing the fluid delivery device 10 to send information back to the remote control device 100. In such an embodiment, the remote control device 100 also includes an integral communication element comprising a receiver and a transmitter, for allowing the remote control device 100 to receive the information sent by the fluid delivery device 10.

The local processor 50 of the device 10 contains all the computer programs and electronic circuitry needed to allow a user to program the desired flow patterns and adjust the program as necessary. Such circuitry can include one or more microprocessors, digital and analog integrated circuits, resistors, capacitors, transistors and other semiconductors and other electronic components known to those skilled in the art. The local processor 50 also includes programming, electronic circuitry and memory to properly activate the dispenser 40 at the needed time intervals.

In the exemplary embodiment of FIG. 2, the device 10 includes a power supply 80, such as a battery or capacitor, for supplying power to the local processor 50. The power supply 80 is preferably integrated into the fluid delivery device 10, but can be provided as replaceable, e.g., a replaceable battery.

Although not shown, the device 10 can include sensors or transducers such as a reservoir volume transducer or a reservoir pressure transducer, for transmitting information to the local processor 50 to indicate how and when to activate the dispenser 40, or to indicate other parameters determining flow, pump flow path prime condition, blockage in flow path, contact sensors, rotary motion or other motion indicators, as well as conditions such as the reservoir 30 being empty or leaking, or the dispensing of too much or too little fluid from the reservoir, etc.

The volume of the reservoir 30 is chosen to best suit the therapeutic application of the fluid delivery device 10 impacted by such factors as available concentrations of medicinal fluids to be delivered, acceptable times between refills or disposal of the fluid delivery device 10, size constraints and other factors. The reservoir 30 may be prefilled by the device manufacturer or a cooperating drug manufacturer, or may include external filling means, such as a fill port having needle insertion septum or a Luer connector, for example. In addition, the device 10 can be provided with a removable reservoir.

The exit port assembly 70 can include elements to penetrate the skin of the patient, such that the entire volume of the flow path 210 of the fluid delivery device 10 is predetermined. For example, a needle-connection tubing terminating in a skin penetrating cannula (not shown) can be provided as an integral part of the exit port assembly 70, with the skin penetrating cannula comprising a rigid member, such as a needle. The exit port assembly 70 can further be provided with injection means, such as a spring driven mechanism, to assist in penetrating the skin with the skin penetrating cannula. For example, if the cannula is a flexible tube, a rigid penetrator within the lumen of the tube can be driven through the skin by the injection means and then withdrawn, leaving the soft cannula in place in the subcutaneous tissue of the patient or other internal site. The injection means may be integral to the device 10, or removable soon after transcutaneous penetration.

Alternatively, the exit port assembly 70 can be adapted to connect, with a Luer connector for example, to a separate, standard infusion device that includes a skin penetrating cannula. In any event, the exit port assembly 70 can also be provided with a removable plug (not shown) for preventing leakage during storage and shipment if pre-filled, and during priming if filled by user, and prior to use. It should be understood that, as used herein, the term "flow path" is meant to include all portions of the fluid delivery device 10 that contain therapeutic fluid for delivery to a patient, e.g., all portions between the fill port of the reservoir to the tip of the needle of the exit port assembly.

Although not shown, the device 10 can also be provided with an adhesive layer on the outer surface of the housing 20 for securing the device 10 directly to the skin of a patient. The adhesive layer is preferably provided in a continuous ring encircling the exit port assembly 70 in order to provide a protective seal around the penetrated skin. The housing 20 can be made from flexible material, or can be provided with flexible hinged sections that allow the fluid delivery device 10 to flex during patient movement to prevent detachment and aid in patient comfort.

Referring to FIGS. 3 through 19 and 22 through 25, the present disclosure provides various combinations of dispensers and reservoirs for use with the fluid delivery device 10 of FIGS. 1 and 2. The dispensers and the reservoirs are small and simple in design, and inexpensive and easy to manufacture, in order to further reduce the size, complexity and costs of the fluid delivery device 10, such that the device 10 continues to lend itself to being small and disposable in nature. In general, the device 10 is provided with non-pressurized reservoirs, and the dispensers are adapted to cause flow from the reservoirs. The dispensers are controlled by the local processor 50, which includes electronic programming, controls, and circuitry to allow sophisticated fluid delivery programming and control of the dispensers.

Figure 3:
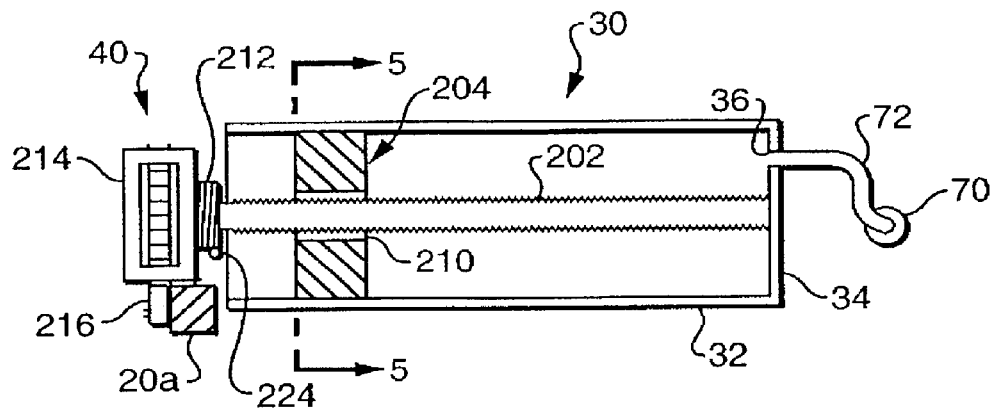
FIG. 3 is a sectional side view of an exemplary embodiment of a reservoir, a plunger and a lead screw of the fluid delivery device of FIG. 1, and an exemplary embodiment of a dispenser constructed in accordance with the present invention for turning the lead screw.
Figure 4:
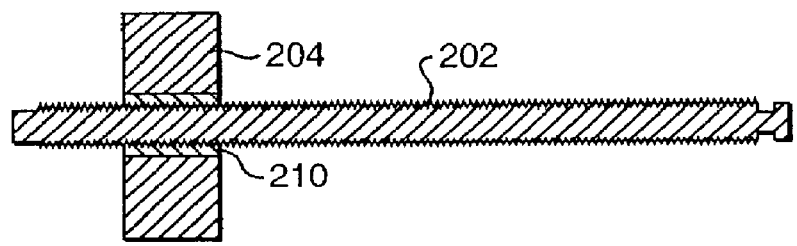
FIG. 4 is an enlarged sectional view of the plunger and the lead screw of the fluid delivery device of FIG. 1.
Figure 5:
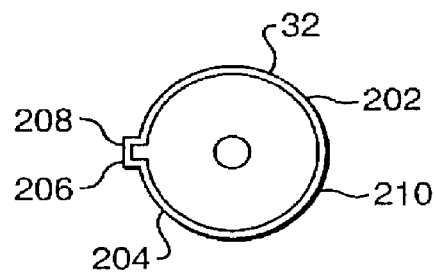
FIG. 5 is a sectional view of the reservoir, the plunger and the lead screw of the fluid delivery device of FIG. 1 taken along line 5—5 of FIG. 3.

Referring to FIGS. 3 through 5, the reservoir 30 is provided with a side wall 32 extending between an open end and an end wall 34 of the reservoir. The end wall 34 includes an outlet 36 connected through a lumen 72 to the exit port assembly 70 of the device 10. The reservoir 30 also includes a threaded lead screw 202 mounted for rotation within the reservoir 30, and a plunger 204 threadedly received on the lead screw. The lead screw 202 is positioned coaxial with the side wall 32 and extends to the end wall 34 of the reservoir 30. The plunger 204 and the reservoir 30 are adapted such that a seal is formed between the plunger 204 and the lead screw 202 and the plunger 204 and the side wall 32 of the reservoir, so that movement of the plunger 204 towards the end wall 34 of the reservoir 30 will force fluid through the outlet 36 to the exit port assembly 70.

The plunger 204 is prevented from rotation with respect to the side wall 32 so that, when the screw 202 is turned with respect to the plunger 204, the plunger is caused to move along the screw 202 within the reservoir 30. In the embodiment shown in FIG. 5, the reservoir 30 and the plunger 204 are provided with circular cross-sections, but the plunger 204 has at least one protrusion 206 radially extending into a channel 208 in the side wall 32 of the reservoir 30 to prevent rotation of the plunger. Alternatively, the plunger 204 can be provided with at least one channel and the side wall 32 of the reservoir 30 can be provided with at least one protrusion extending along its length and received within the channel of the plunger to prevent rotation of the plunger. In addition, the reservoir 30 and the plunger 204 can alternatively be provided with corresponding non-circular cross-sections, such as oval, square or rectangular, to prevent rotation of the plunger 204 with respect to the side wall, without the use of a protrusion and a channel. Such non-circular cross-sections can also include simply providing the side wall and the plunger with mating flat portions in otherwise circular cross-sections.

An advantage of the reservoir 30 of FIGS. 3 through 5 is that it utilizes an integrated lead screw 202 that extends to the end wall 34 of the reservoir, and thus has an overall length reduction as compared to a syringe having a reservoir with a separate sliding plunger and lead screw extending out of the open end of the reservoir. Another advantage of the reservoir 30 is that the plunger 204 and the internal lead screw 202 are entirely contained within the reservoir 30, and do not require mechanisms or procedures for pulling the plunger back to remove a used syringe or re-load a full syringe. Such mechanisms or procedures can increase the costs, complexity, and size and weight, and decrease the reliability of a fluid delivery device. Thus, the reservoir 30 FIGS. 3 through 5 advantageously does not need such mechanisms or procedures.

In order to further reduce the cost of the reservoir 30, the lead screw 202 and the plunger 204 are preferably made from an inexpensive material. The lead screw 202 is made of a rigid material such as a metal, such as stainless steel, or a plastic, such as polyethylene or polypropylene. The side wall 32 and the end wall 34 of the reservoir are preferably made from a rigid material such as a suitable metal (e.g., stainless steel) or plastic. The plunger 204, however, is made of a flexible material, such as a silicone elastomer or rubber, and provided with a rigid insert 210 made of metal or plastic for engaging the threads of the lead screw 202. Since the device is preferably disposable, preventing thread wear between the lead screw 202 and the plunger 204 is not necessary, thereby allowing the use of less expensive materials and lower tolerances in the manufacture and assembly of the lead screw 202 and the plunger 204.

Figure 6:
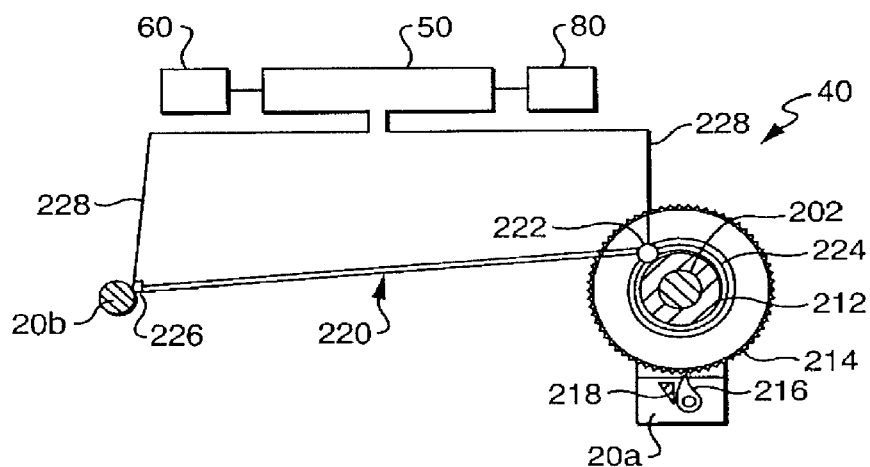
FIG. 6 is an end elevation view, partially in section, of the dispenser for turning the lead screw of the fluid delivery device of FIG. 1.

Referring also to FIG. 6, the dispenser 40 causes fluid flow by turning the lead screw 202 of the reservoir 30. In the embodiment of FIGS. 3 and 6, the dispenser 40 includes a hub 212 coaxially fixed to the lead screw 202, such that rotation of the hub causes rotation of the lead screw. Coaxially secured to the hub 212 is a gear 214 having radially extending teeth. The lead screw 202 and the plunger 204 are adapted such that rotation of the lead screw in a first direction, which is counter-clockwise as shown in FIG. 6, causes movement of the plunger 204 towards the end wall 34 of the reservoir 30 to force fluid through the outlet 36 to the exit port assembly 70. The dispenser also includes a pawl 216 pivotally mounted on a fixed member 20a of the housing 20 of the fluid delivery device 10. The pawl 216 engages the teeth of the gear 214 and is arranged with a backstop 218 to prevent rotation of the gear 214, the hub 212 and the lead screw 202 in a second direction, which is clockwise as shown in FIG. 6.

The exemplary embodiment of the dispenser 40 of the present invention also includes a shape memory element 220 made of a shape memory material. The application of an electrical current to a shape memory material results in molecular and crystalline restructuring of the shape memory material. If the shape memory material is in the shape of an elongated wire, for example, as the shape memory element 220 preferably is, this restructuring causes a decrease in length. Nitinol, a well-known alloy of nickel and titanium, is an example of such a so-called shape memory material and is preferred for use as the shape memory element 220.

As shown best in FIG. 6, a first end 222 of the shape memory element 220 is secured to the hub 212, a portion 224 of the shape memory element 220 is wrapped around the hub 212, and a second end 226 of the shape memory element 220 is secured to a fixed internal portion of the housing 20 of the fluid delivery device 10. The dispenser 40 includes wires 228 connecting the opposite ends 222, 226 of the shape memory element 220 to the processor 50 of the fluid delivery device. When a charge is applied to the shape memory element 220 through the wires 228, the length of the shape memory element 220 decreases from an uncharged length to a charged length. The decrease in length occurs with a force that is sufficient to rotate the hub 212 and the lead screw 202 in the first direction to advance the plunger 204. The dispenser 40 does not include means for pulling the shape memory element 220 back to its original length upon the charge being removed from the element.

Although not shown, the processor 50 can include capacitors for storing a charge received from the power source 80. The fluid delivery device 10 is calibrated so that a single charge from the processor 50 causes the dispensing of a predetermine volume of fluid, called pulse volume (PV), from the reservoir 30. In this manner, a desired volume to be delivered by the fluid delivery device 10 is dispensed by the release of multiple charges over a predetermined period. PV's delivered by infusion devices are typically chosen to be small relative to what would be considered a clinically significant volume. For insulin applications at a concentration of one hundred units per microliter (100 units/ml), a PV of less than two microliters, and typically a half of a microliter, is appropriate. If the fluid delivery device 10 is programmed via the remote control device 100 to deliver two units an hour, the processor 50 will deliver forty charges an hour, or a charge every ninety seconds, to the shape memory element 220. Other drugs or concentrations may permit a much larger PV. Various flow rates are achieved by adjusting the time between charges. To give a fixed volume or bolus, multiple charges are given in rapid succession until the bolus volume is reached.

Figure 7:
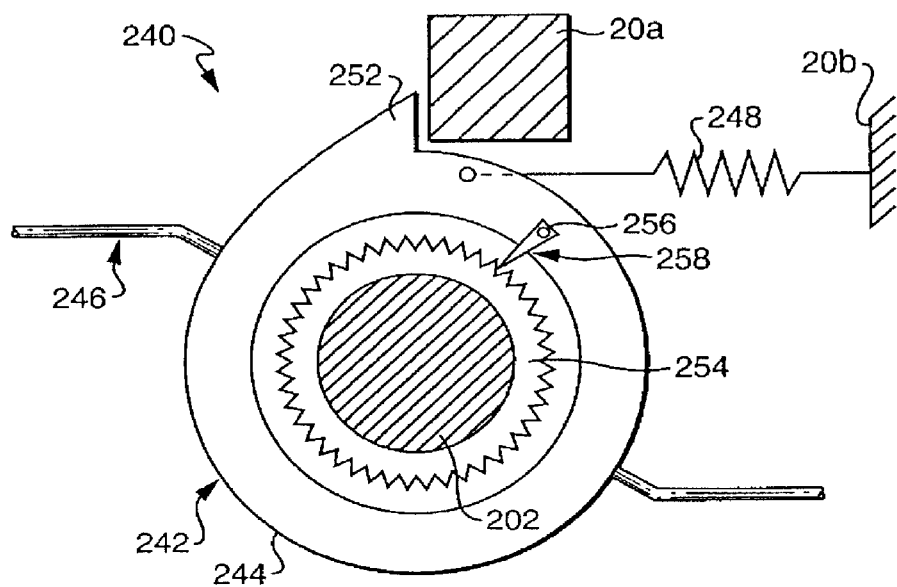
FIG. 7 is a first end elevation view, partially in section, of another exemplary embodiment of a dispenser constructed in accordance with the present invention for turning the lead screw of the fluid delivery device of FIG. 1.
Figure 8:
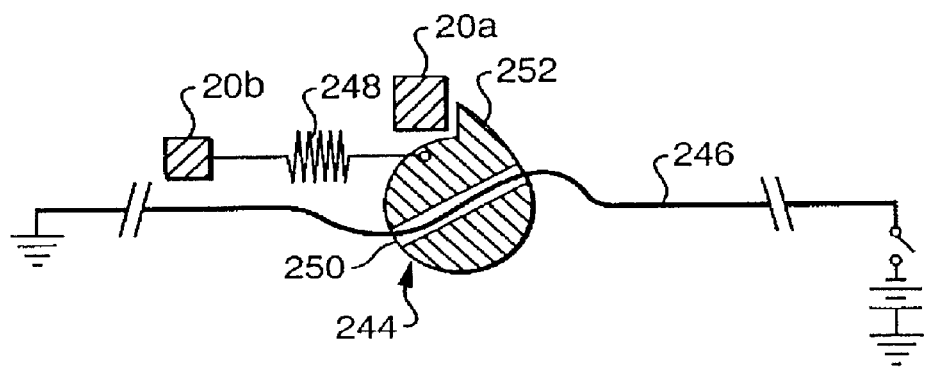
FIGS. 8 and 9 are schematic second end elevation views illustrating operation of the dispenser of FIG. 7.
Figure 9:
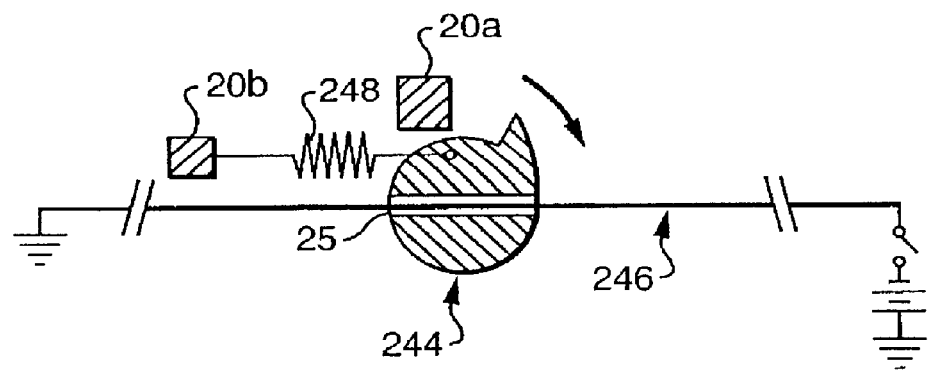

Another exemplary embodiment of a dispenser 240 constructed in accordance with the present invention is shown in FIGS. 7 through 9. The dispenser 240 includes a ratchet mechanism 242 secured to the lead screw 202 and including a wheel 244 arranged such that rotation of the wheel in a first direction (which is clockwise as shown in FIG. 7 and counter-clockwise as shown in FIGS. 8 and 9) causes rotation of the lead screw 202 in the first direction, while rotation of the wheel 244 in a second direction (which is counter-clockwise as shown in FIG. 7 and clockwise as shown in FIGS. 8 and 9) causes no rotation of the lead screw 202.

The dispenser 240 also includes an elongated shape memory element 246 operatively connected to the wheel 244 of the ratchet mechanism 242 such that the changeable length of the shape memory element 246 decreasing from an uncharged length to a charged length causes rotation of the wheel 244 in one of the first direction and the second direction. An actuation element 248 is secured to the wheel 244 for moving the wheel in the other of the first direction and the second direction.

In the embodiment shown in FIGS. 7 through 9, the actuation element comprises a spring 248. The spring 248 biases the wheel 244 in the second direction, while the changeable length of the shape memory element 246 decreasing from an uncharged length to a charged length overcomes the biasing force of the spring 248 and causes rotation of the wheel 244 in the first direction. As shown best in FIGS. 8 and 9, the spring is a helical tension spring 248 that expands upon the shape memory element 246 decreasing from an uncharged length to a charged length, and contracts to increase the shape memory element 246 from a charged length to an uncharged length.

The shape memory element 246 comprises an elongated wire that extends through a traverse passage 250 in the wheel 244, and the spring 248 normally biases the wheel such that an uncharged length of the shape memory element is bent, as shown in FIG. 8. The shape memory element 246 decreasing from an uncharged length to a charged length straightens the charged length of the shape memory element and rotates the wheel 244 in the first direction against the bias of the spring 248, as shown in FIG. 9. When the charge is removed, the spring 248 biases the wheel 244, increases the length of the shape memory element 246 to the uncharged length, and bends the uncharged length of the shape memory element, as shown in FIG. 8.

The dispenser 240 preferably includes means for limiting rotation of the wheel 244 in the first direction. In particular, the wheel 244 includes a radially extending tooth 252 positioned to contact a first fixed member 20a of the device housing and limit rotation of the wheel 244 in the first direction. The spring 248 extends between the wheel 244 and a second fixed member 20d of the device housing and normally pulls the tooth 252 against the first fixed member 20a.

As shown best in FIG. 7, the ratchet mechanism 242 further includes a gear 252 secured to the lead screw 202 coaxially within the wheel 244 and having teeth extending radially outwardly towards the wheel. A pawl 256 is pivotally mounted on the wheel 244 and extends radially inwardly from the wheel and engages the teeth of the gear 252. A backstop 258 limits pivotal motion of the pawl 256 to prevent relative rotation between the wheel 244 and the gear 252 during rotation of the wheel in the first direction, and allow relative rotation between the wheel and the gear during rotation of the wheel 244 in the second direction. In this manner rotation of the wheel 244 in the first direction causes rotation of the gear 252 and the lead screw 202 (and advancement of the plunger), while rotation of the wheel 244 in the second direction does not cause rotation of the lead screw 202.

Figure 10:
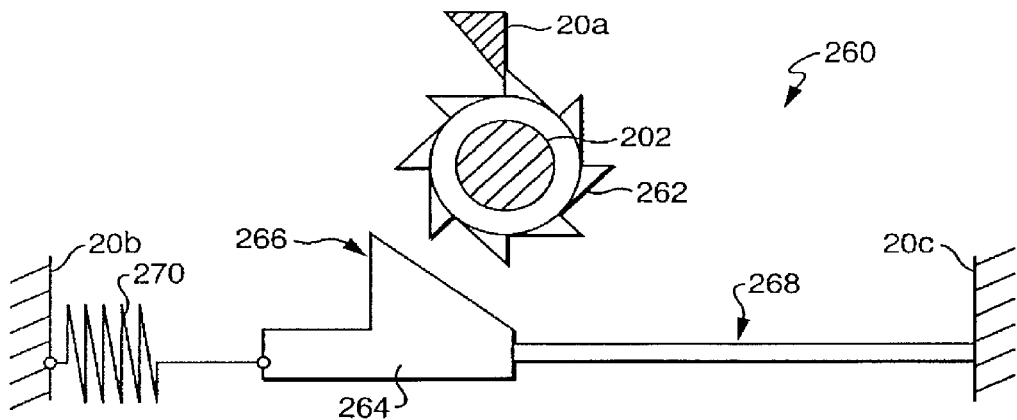
FIGS. 10 through 12 are schematic end elevation views, partially in section, illustrating operation of an additional exemplary embodiment of a dispenser constructed in accordance with the present invention for turning the lead screw of the fluid delivery device of FIG. 1.
Figure 11:
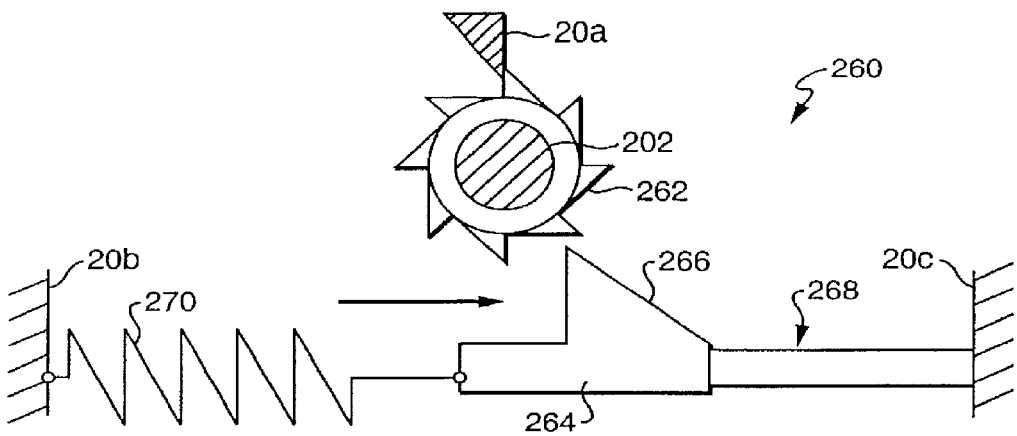
Figure 12:
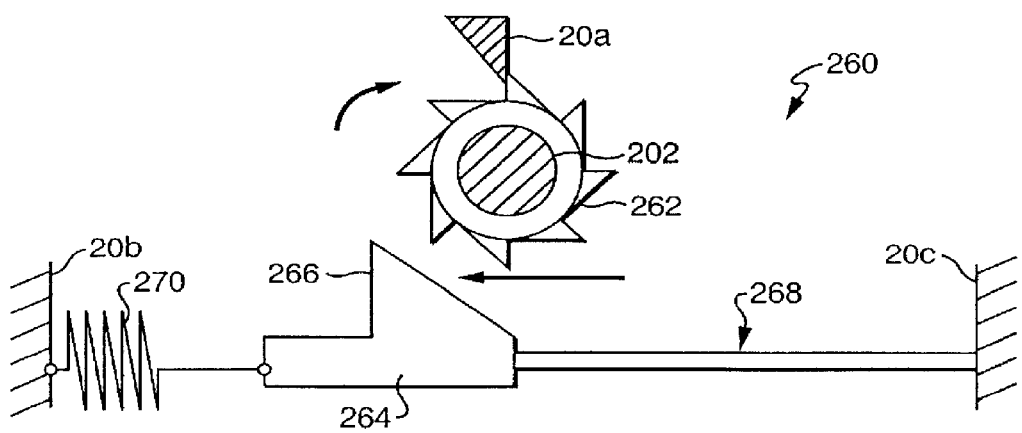

An additional exemplary embodiment of a dispenser 240 constructed in accordance with the present invention is shown in FIGS. 10 through 12. The dispenser 240 includes a gear 262 secured to the lead screw 202 and including radially extending teeth positioned to contact a first fixed member 20a of the device housing and prevent rotation of the gear 262 and the lead screw 202 in the second direction (which is counter-clockwise as shown in FIGS. 10 through 12). A slide 264 is positioned for linear movement adjacent the gear 262 between a second fixed member 20b and a third fixed member 20c. The slide 264 includes a finger 266 for engaging the teeth of the gear 262, and the finger and the teeth are adapted such that linear movement of the slide 264 past the gear 262 towards the second fixed member 20b, as shown in FIG. 12, causes rotation of the gear 262 in the first direction (which is clockwise as shown in FIGS. 10 through 12). The finger 266 and the teeth of the gear 262 are also adapted such that linear movement of the slide 264 past the gear towards the third fixed member 20c, as shown in FIG. 11, causes no rotation of the gear (i.e., the finger and the teeth are shaped to slide over each other as the slide 264 moves past the gear 262 towards the third fixed member 20c).

The dispenser also includes an elongated shape memory element 268 connected between the slide 264 and the third fixed member 20c, such that the changeable length of the shape memory element 268 decreasing from an uncharged length to a charged length causes linear movement of the slide 264 past the gear 262 towards the third fixed member 20c, as shown in FIG. 11. An actuation element 270 is connected between the slide 264 and the second fixed member 20b for causing linear movement of the slide 264 past the gear 262 towards the second fixed member 20b when the shape memory element 268 increases from a charged length to an uncharged length, as shown in FIG. 12. The actuation element 270, therefore, rotates the lead screw 202 in the first direction (and advances the piston in the reservoir to dispense fluid to the exit port assembly).

In the embodiment of FIGS. 10 through 12, the actuation element comprises a spring 270. Preferably, the spring is a helical tension (or extension) spring 270 that expands upon the shape memory element 268 decreasing from an uncharged length to a charged length, and contracts to increase the shape memory element 268 from a charged length to an uncharged length.

Figure 13:
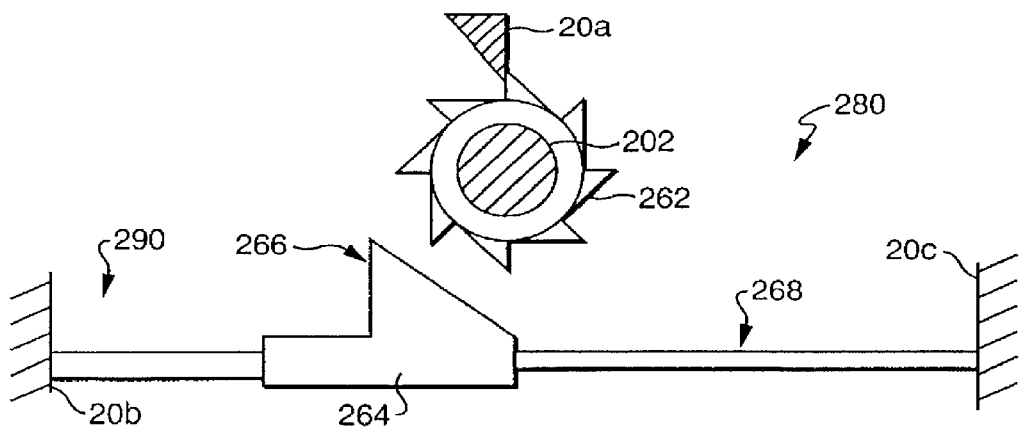
FIGS. 13 through 15 are schematic end elevation views, partially in section, illustrating operation of a further exemplary embodiment of a dispenser constructed in accordance with the present invention for turning the lead screw of the fluid delivery device of FIG. 1.
Figure 14:
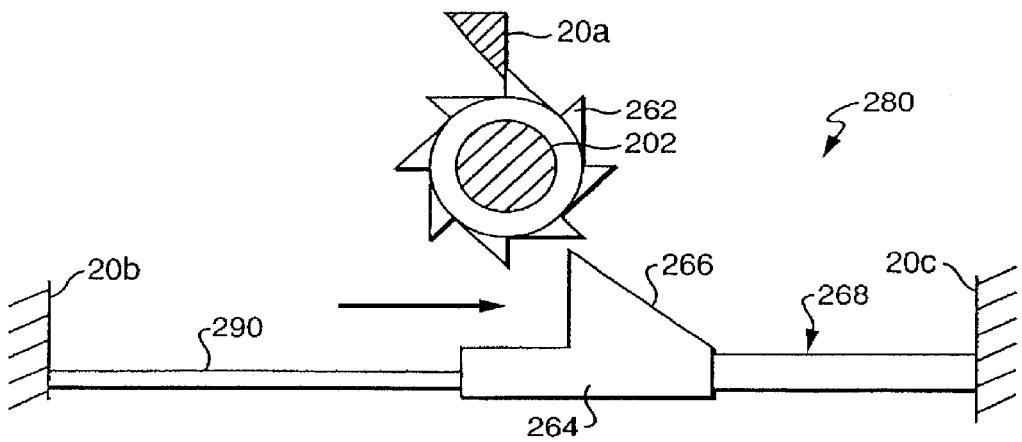
Figure 15:
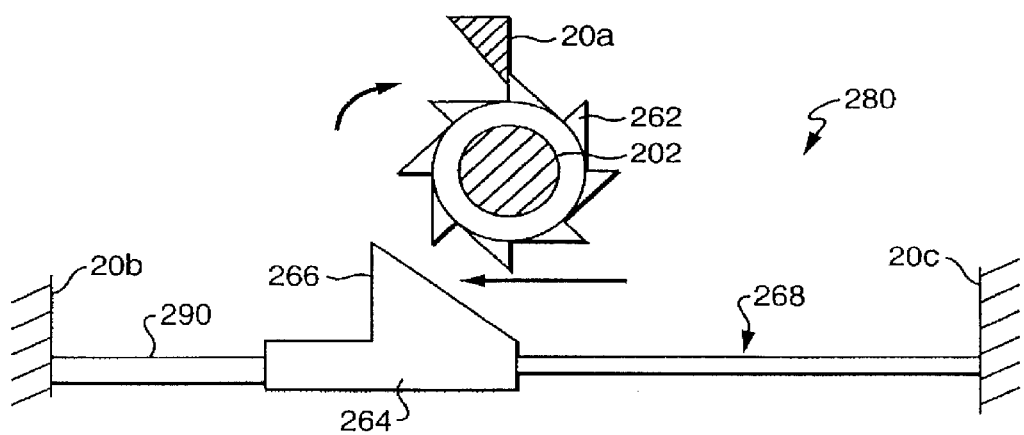

A further exemplary embodiment of a dispenser 280 constructed in accordance with the present invention is shown in FIGS. 13 through 15. Operation of the dispenser 280 is similar to operation of the dispenser 260 of FIGS. 10 through 12. In addition, elements of the dispenser 280 are similar to elements of the dispenser 260 of FIGS. 10 through 12 such that similar elements have the same reference numeral. In the embodiment 280 of FIGS. 13 through 15, however, the actuation element comprises a second elongated shape memory element 290. The second shape memory element 290 is connected between the slide 264 and the second fixed member 20b such that the changeable length of the second shape memory element 290 decreasing from an uncharged length to a charged length causes linear movement of the slide 264 past the gear 262 towards the second fixed member 20b. The (first) shape memory element 268 and the second shaped memory element 290 are alternatively charged to cause linear motion of the slide 264 and rotation of the gear 262 and the lead screw 202.

Still another exemplary embodiment of a dispenser 300 constructed in accordance with the present invention is shown in FIGS. 16 through 19. The dispenser 300 includes a gear 302 secured to the lead screw 202 and having radially extending teeth positioned to contact a first fixed member 20a of the device housing and prevent rotation of the gear 302 and the lead screw 202 in the second direction. A slide 304 is positioned for linear movement between the gear 302 and a second fixed member 20b. The slide 304 includes a finger 306 for engaging the teeth of the gear 302, and the finger 306 and the teeth are adapted such that linear movement of the slide 304 towards the gear 302, as shown in FIGS. 17 and 18, causes rotation of the gear 302 in the first direction while linear movement of the slide 304 towards the second fixed member 20b, as shown in FIG. 19, causes no rotation of the gear 302.

The dispenser 300 of FIGS. 16 through 19 also includes an elongated shape memory element 308 connected between the slide 304 and the second fixed member 20b such that the changeable length of the shape memory element 308 decreasing from an uncharged length to a charged length causes linear movement of the slide 304 towards the second fixed member 20b. An actuation element 310 is connected between the slide 304 and the second fixed member 20b for causing linear movement of the slide 304 towards the gear 302 when the shape memory element 308 is uncharged. As shown, the actuation element comprises a helical compression spring 310 that contracts upon the shape memory element 308 decreasing from an uncharged length to a charged length, and expands to increase the shape memory element 308 from a charged length to an uncharged length.

The dispenser 300 further includes a latch 312 movable between the slide 304 and a third fixed member 20c. The latch 312 is adapted and arranged to engage a shoulder 314 of the slide 304, when the latch 312 is moved to the slide 304, to prevent movement of the slide 304 towards the gear 302. A second elongated shape memory element 316 is connected between the latch 312 and the third fixed member 20c such that the changeable length of the second shape memory element 316 decreasing from an uncharged length to a charged length causes movement of the latch 312 towards the third fixed member 20c.

A second actuation element 318 is connected between the latch 312 and the third fixed member 20c for causing movement of the latch 312 towards the slide 304 when the second shape memory element 316 is uncharged. As shown, the second actuation element also comprises a helical compression spring 318 that contracts upon the second shape memory element 316 decreasing from an uncharged length to a charged length, and expands to increase the second shape memory element 316 from a charged length to an uncharged length.

During operation, the second shaped memory element 316 is charged to pull the latch 312 off the shoulder 314 of the slide 304, as shown in FIG. 17, and allow the first spring 310 to bias the slide 304 towards the gear 302 and rotate the gear 302 and the lead screw 202 in the first direction, as shown in FIG. 18. Thus, the first spring 310 actually causes rotation of the lead screw 202 (and advancement of the piston).

Then, as shown in FIG. 19, a charge is applied to the first shape memory element 308 to pull the slide 304 away from the gear 302 and back towards the second fixed member 20b such that the shoulder 314 of the slide 304 falls below the level of the latch 312. The charge is then removed from the second shape memory element 316, such that the second spring 318 is allowed to move the latch 312 towards the slide 304 and over the shoulder 314, as shown in FIG. 16. Thereafter, the charge can be removed from the first shape memory element 308 since the shoulder 314 caught by the latch 312 will prevent the first spring 310 from moving the slide 304 to the gear 302. The steps illustrated in FIGS. 16 through 19 are successively repeated (through electrical charges provided by the local processor) to produce pulse volumes of fluid flow from the reservoir.

An end of the shape memory element of any of the above described dispensers can be connected to an auxiliary component of the fluid delivery device 10 for actuating the auxiliary component upon at least a first charge applied to the shape memory element. For example, the auxiliary component can comprise a spring-loaded needle of the exit port assembly and the shape memory element can be arranged to release the spring-loaded needle for insertion into a patient upon first decreasing from an uncharged length to a charged length when a first, or initial, charge is applied to the shape memory element.

Figure 20:
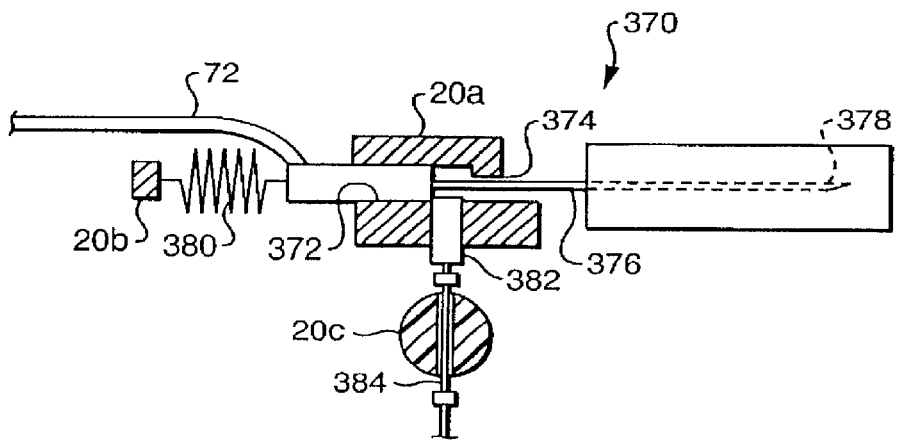
FIGS. 20 and 21 are top plan views, partially in section, of exemplary embodiment of an auxiliary component constructed in accordance with the present invention, illustrating actuation of the component.
Figure 21:
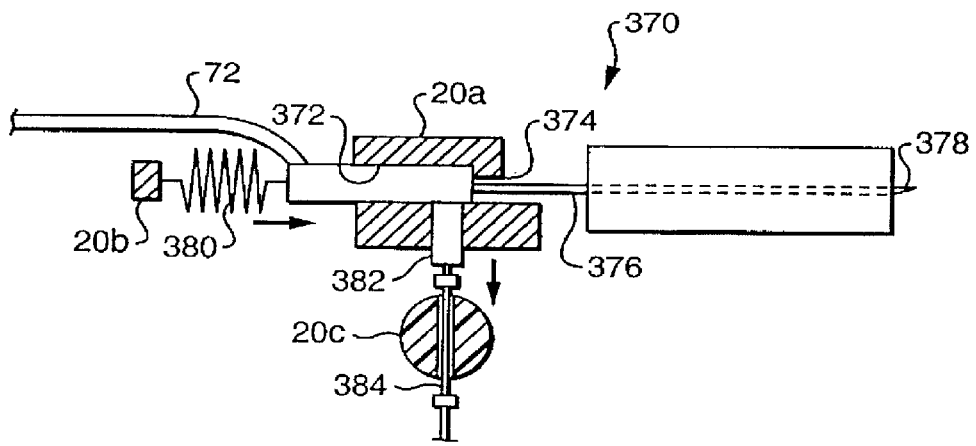

FIGS. 20 and 21 show an exemplary embodiment of an auxiliary component 70 constructed in accordance with the present invention for use with the shape memory elements of the dispensers disclosed herein. The auxiliary component is provided in the form of an exit port assembly 70 including a fixed member 20a of the device housing defining a channel 372 having an outlet 374, and a transcutaneous patient access tool 376 received for sliding movement in the channel 372 towards the outlet 374. In the embodiment shown, the transcutaneous patient access tool comprises a rigid needle 376 having a sharpened, hollow end 378.

The exit port assembly 370 also includes an actuation element 380 connected between the tool 376 and a second fixed member 20b for causing sliding movement of the tool towards the outlet 374 of the channel 372. In the embodiment shown, the actuation element comprises a helical compression spring 380 that expands to cause sliding movement of the needle 376 towards the outlet 374 of the channel 372.

A latch 382 is removably positioned within the channel 372 between the needle 376 and the outlet 374 to prevent the spring 380 from moving the needle to the outlet, as shown in FIG. 20. An elongated shape memory element 384 is connected to the latch 382 such that the changeable length of the shape memory element 384 decreasing from an uncharged length to a charged length causes movement of the latch 382 out of the channel 372 and release of the needle 376, as shown in FIG. 21. The elongated shaped memory element 384 preferably comprises the elongated shaped memory element of a dispenser, such as the dispensers disclosed herein, of the fluid delivery device, such that a single elongated shaped memory element is used to operate two components of the device.

Figure 22:
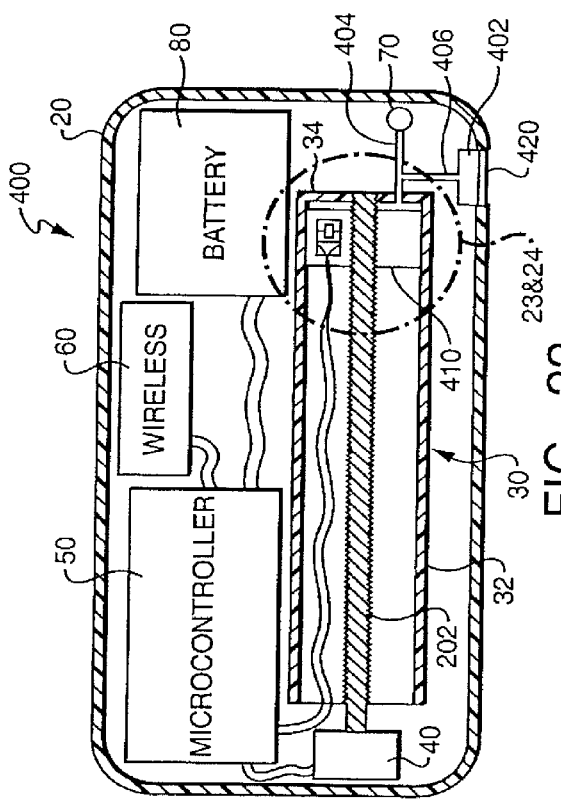
FIG. 22 is a top plan sectional view of another exemplary embodiment of a fluid delivery device constructed in accordance with the present invention.
Figure 24:
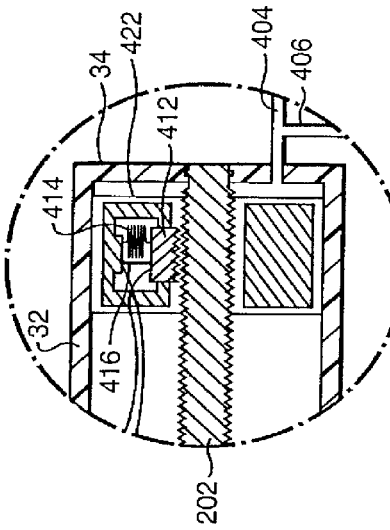
FIGS. 23 and 24 are enlarged views of the portion of the fluid delivery device contained in circle "23 & 24" of FIG. 22 illustrating operation of a plunger of the device.
Figure 23:
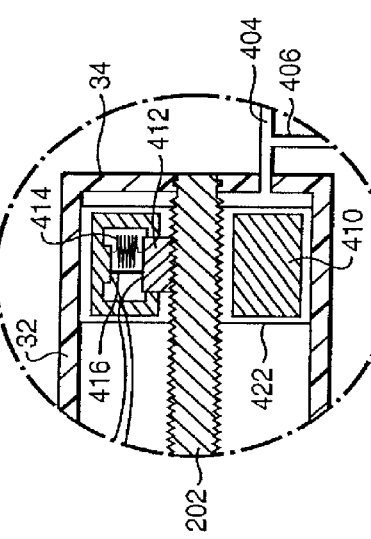

FIGS. 22 through 24 show another exemplary embodiment of a fluid delivery device 400 constructed in accordance with the present invention. Operation of the device 400 of FIG. 22 is similar to the operation of the device 10 of FIGS. 1 and 2, and similar elements have the same reference numeral.

Referring to FIG. 22, the device 400 includes an exit port assembly 70, a fill port 402, and a reservoir 30 including a side wall 32 extending towards an outlet 404 connected to the exit port assembly 70 and an inlet 406 connected to the fill port 402. A threaded lead screw 202 is received in the reservoir 30 and extends towards the outlet 404 and the inlet 406, generally parallel with the side wall 32, and a plunger 410 has an outer periphery slidably received on the side wall 32 of the reservoir 30 and an inner periphery slidably received on the lead screw 202.

Referring also to FIGS. 23 and 24, the plunger 410 is non-rotatable with respect to the side wall 32 and includes an insert 412 having a threaded surface mateable with the threaded lead screw 202, and a spring 414 biasing the threaded surface of the insert 412 against the threaded lead screw 202, as shown in FIG. 23, such that rotating the lead screw 202 in a first direction causes the plunger 410 to slide along the side wall 32 towards the outlet 404 of the reservoir 30. The plunger 410 also includes an elongated shape memory element 416 having a first end secured to the insert 412 and a second end extending radially outwardly from the insert 412 and secured to the plunger 410, such that the changeable length of the shape memory element 416 decreasing from an uncharged length to a charged length pulls the threaded surface of the insert 412 away from the threaded lead screw 202, as shown in FIG. 24.

Thus, when no charge is applied to the shape memory element 416, the insert 412 engages the lead screw 202 as shown in FIG. 23. Applying a charge to the shape memory element 416, however, disengages the insert 412 from the lead screw 202, as shown in FIG. 24, and allows the plunger 410 to slide along the lead screw 202 and away from the inlet 406 of the reservoir 30 during filling of the reservoir through the fill port 402.

The device 400 also includes a dispenser 40 operatively connected to the lead screw 202 for rotating the lead screw to advance the plunger 410 towards the outlet 404 of the reservoir 30. The dispenser can comprise a rotary motor 40 mated to an end of the lead screw 202 and controlled by the local processor 50 of the device 400. As shown, the local processor 50 is also connected to the ends of the shape memory element 416, through wires 418, for controlling the shape memory element by applying or removing a charge to the shape memory element.

In the embodiment shown in FIG. 22, the fill port 402 includes a needle-pierceable septum 420. Although not shown, the device 400 can further include a sensor, such as a pressure switch, connected to the local processor 50 and adapted and arranged to provide a signal upon the presence of a needle in the fill port 402. The local processor 50, in-turn, can be programmed to apply a charge to the shape memory element 416 of the plunger 410 whenever it receives a signal from the fill port sensor. Thus when a needle is positioned in the fill port 402, the plunger insert 412 is disengaged from the lead screw 202 to allow the plunger 410 to slide on the lead screw 202, away from the inlet 406, upon fluid being added to the reservoir 30 through a needle inserted into the fill port 402. Alternatively, the device 400 can be provided with a manual actuator, such as a button for a user to push, for applying a charge to the shape memory element 416 during a filling process.

As shown best in FIGS. 23 and 24, the plunger 410 preferably includes an outer layer 422 of resiliently flexible material providing a substantially fluid-tight interface between the outer periphery of the plunger 410 and the side wall 32 of the reservoir 30 and the inner periphery of the plunger 410 and the lead screw 202.

Figure 25:
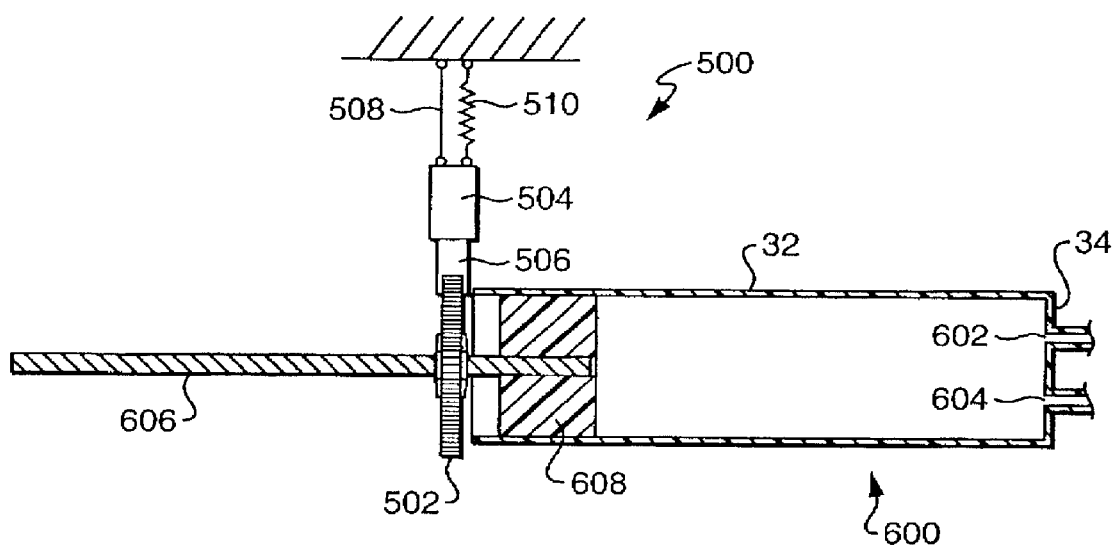
FIG. 25 is a side elevation view, partially in section, of still other exemplary embodiments of a dispenser and a reservoir constructed in accordance with the present invention for use as part of a fluid delivery device, such as the fluid delivery device of FIG. 1.

Referring to FIG. 25, another dispenser 500 and reservoir 600 constructed in accordance with the present invention for use with a fluid delivery device, such as the fluid delivery device 10 of FIGS. 1 and 2, are shown. The reservoir 600 is provided with a side wall 32 extending between an open end and an end wall 34 of the reservoir. The end wall 34 includes an outlet 602 for connection to the exit port assembly of the device, and an inlet 604 for connection to a fill port of the device. The reservoir 600 also includes a threaded lead screw 606 extending into the reservoir, and a plunger 608 secured to an end of the lead screw. The plunger 608 and the reservoir 600 are adapted such that a seal is formed between the plunger 608 and the lead screw 606 and the plunger and the side wall 32, so that movement of the plunger towards the end wall 34 of the reservoir 600 will force fluid through the outlet 602 to the exit port assembly.

The dispenser 500 causes fluid flow by causing linear movement of the lead screw 606 and the plunger 608 towards the outlet of the reservoir 30. In the embodiment of FIG. 25, the dispenser 500 includes a rotatable gear 502 linearly fixed with respect to the reservoir 600. The gear 502 is coaxially mounted with respect to the lead screw 606, and is threadedly engageable with the lead screw 606, such that rotation of the gear 502 causes linear movement of the lead screw. In particular, the lead screw 606 and the gear 502 are adapted such that rotation of the gear 502 in a first direction causes linear movement of the lead screw 606 and the plunger 608 towards the end wall 34 of the reservoir 600 to force fluid through the outlet 36 to the exit port assembly.

The dispenser 500 of FIG. 25 also includes a slide 504 having a finger 506 for successively engaging teeth of the gear 502, similar to the slide 304 and the finger 306 of the dispenser 300 of FIGS. 16 through 19. The dispenser 500 additionally includes a combination of a shape memory element 508 and a spring 510, similar to the shape memory element 308 and the spring 310 of the dispenser 300 of FIGS. 16 through 19, for causing the slide 504 and the finger 506 to successively rotate the gear 502 to advance the lead screw 606 and the plunger 608.

Although not shown, the gear 502 of FIG. 25 is configured similar to the plunger 410 of FIGS. 22 through 24 so that the gear 502 can be released from the lead screw 606 to allow the lead screw 606 and the plunger 608 to be linearly moved away from the inlet 604 of the reservoir 600 during filling of the reservoir. In particular, the gear 502 includes an insert having a threaded surface mateable with the threaded lead screw 606, and a spring biasing the threaded surface of the insert against the threaded lead screw 606. The gear 502 also includes an elongated shape memory element having a first end secured to the insert and a second end extending radially outwardly from the insert and secured to the gear 502, such that the changeable length of the shape memory element decreasing from an uncharged length to a charged length pulls the threaded surface of the insert away from the threaded lead screw 606. Thus, when no charge is applied to the shape memory element, the insert engages the lead screw 606. Applying a charge to the shape memory element, however, disengages the insert of the gear 502 from the lead screw 606 and allows the lead screw 606 to move linearly with respect to the gear 502 during filling of the reservoir through the inlet.

As illustrated by the above described exemplary embodiments, the present invention generally provides a device for delivering fluid, such as insulin for example, to a patient. The device includes an exit port assembly, a syringe-like reservoir including a side wall extending towards an outlet connected to the exit port assembly. A threaded lead screw is received in the reservoir and a plunger has an outer periphery linearly slideable along the side wall of the reservoir and an inner periphery threadedly received on the lead screw. The plunger is non-rotatable with respect to the side wall such that rotating the lead screw causes the plunger to advance within the reservoir and force fluid through the outlet. The device also includes a dispenser having a shape memory element, and a changeable length of the shape memory element decreasing from an uncharged length to a charged length causes rotation of the lead screw.

It should be understood that the embodiments described herein are merely exemplary and that a person skilled in the art may make variations and modifications to the embodiments described without departing from the spirit and scope of the present invention. All such equivalent variations and modifications are intended to be included within the scope of this invention as defined by the appended claims.

What is claimed is:

1. A device for delivering fluid to a patient, comprising:
an exit port assembly;
a reservoir including a side wall extending towards an outlet connected to the exit port assembly;
a threaded lead screw received at least partly in the reservoir and extending towards the outlet;
a plunger secured to the lead screw and having an outer periphery linearly slideable along the side wall of the reservoir, wherein the plunger and the lead screw are operatively arranged such that rotating the lead screw in a first direction causes the plunger to slide along the side wall towards the outlet of the reservoir;
a dispenser including an elongated shape memory element having a changeable length decreasing from an uncharged length to a charged length when at least one charge is applied to the shape memory element, the shape memory element having a first end secured to the lead screw, a portion of the elongated shape memory element wrapped around the lead screw, and a second end fixed with respect to the lead screw, such that the changeable length of the shape memory element decreasing from an uncharged length to a charged length causes rotation of the lead screw in the first direction.

2. A device according to claim 1, wherein the dispenser further includes a gear secured to the lead screw, and a pawl engaging the gear to prevent rotation of the lead screw in a second direction yet allow rotation of the lead screw in the first direction.

3. A device according to claim 1, wherein the shape memory element comprises a wire.

4. A device according to claim 1, wherein the elongated shape memory element is made of a nickel and titanium alloy.

5. A device according to claim 1, wherein the plunger is non-rotatable with respect to the side wall of the reservoir.

6. A device according to claim 5, wherein the side wall of the reservoir and the plunger have a non-circular cross-section.

7. A device according to claim 5, wherein the side wall of the reservoir includes a channel extending parallel with the lead screw, and the plunger includes a protrusion slidingly received in the channel.

8. A device according to claim 1, wherein:
the reservoir includes an end wall defining the outlet connected to the exit port assembly;
the threaded lead screw extends to the end wall; and
the plunger is non-rotatable with respect to the side wall of the reservoir and is rotatably mounted on the lead screw.

9. A device according to claim 8, wherein the plunger includes an insert threadedly received on the lead screw and wherein the threaded insert and the plunger are made from different materials.

10. A device according to claim 1, further comprising:
a local processor connected to the ends of the shape memory element and programmed to provide charges to the shape memory element based upon flow instructions;
a wireless receiver connected to the local processor for receiving flow instructions from a separate, remote control device and delivering the flow instructions to the local processor; and a housing containing the reservoir, the exit port assembly, the dispenser, the local processor and the wireless receiver, wherein the housing is free of user input components for providing flow instructions to the local processor.

11. A system including a fluid delivery device according to claim 10, and further comprising a remote control device separate from the fluid delivery device and including:

a remote processor;

user interface components connected to the remote processor for allowing a user to provide flow instructions to the remote processor; and a transmitter connected to the remote processor for transmitting the flow instructions to the receiver of the fluid delivery device.

12. A device according to claim 1, wherein the reservoir contains a therapeutic fluid.

13. A device according to claim 12, wherein the therapeutic fluid is insulin.

14. A device according to claim 1, wherein the exit port assembly includes a transcutaneous patient access tool.

15. A device according to claim 14, wherein the transcutaneous patient access tool comprises a needle.

16. A device according to claim 1, wherein the second end of the shape memory element is connected to an auxiliary component of the fluid delivery device for actuating the auxiliary component upon at least a first charge applied to the shape memory element.

17. A device according to claim 16, wherein the auxiliary component comprises a spring-loaded needle of the exit port assembly and the shape memory element is arranged to release the spring-loaded needle for insertion into a patient upon first decreasing from an uncharged length to a charged length when the first charge is applied to the shape memory element.

18. A device according to claim 1, further comprising a local processor connected to the ends of the shape memory element and programmed to provide charges to the shape memory element based upon flow instructions.

19. A device according to claim 18, further comprising a power supply connected to the local processor.

20. A device for delivering fluid to a patient, comprising:

an exit port assembly;

a reservoir including a side wall extending towards an outlet connected to the exit port assembly;

a threaded lead screw at least partly received in the reservoir and extending towards the outlet;

a plunger secured to the lead screw and having an outer periphery linearly slideable along the side wall of the reservoir, wherein the plunger and the lead screw are operatively arranged such that rotation of the lead screw in a first direction causes the plunger to slide along the side wall towards the outlet of the reservoir; and a dispenser including, a ratchet mechanism secured to the lead screw and including a wheel arranged such that rotation of the wheel in the first direction causes rotation of the lead screw in the first direction, while rotation of the wheel in a second direction causes no rotation of the lead screw, an elongated shape memory element having a changeable length decreasing from an uncharged length to a charged length when at least one charge is applied to the shape memory element, the shape memory element operatively connected to the wheel of the ratchet mechanism such that the changeable length of the shape memory element decreasing from an uncharged length to a charged length causes rotation of the wheel in one of the first direction and the second direction, and an actuation element secured to the wheel for moving the wheel in the other of the first direction and the second direction.

21. A device according to claim 20, wherein the actuation element comprises a spring.

22. A device according to claim 21, wherein the spring biases the wheel in the second direction, while the changeable length of the shape memory element decreasing from an uncharged length to a charged length overcomes the biasing force of the spring and causes rotation of the wheel in the first direction.

23. A device according to claim 22, wherein the spring is a helical tension spring that expands upon the shape memory element decreasing from an uncharged length to a charged length, and contracts to increase the shape memory element from a charged length to an uncharged length.

24. A device according to claim 23, wherein the shape memory element extends through a traverse passage in the wheel, the spring biases the wheel such that an uncharged length of the shape memory element is bent, and the shape memory element decreasing from an uncharged length to a charged length straightens the charged length of the shape memory element and rotates the wheel in the first direction against the bias of the spring.

25. A device according to claim 24, further comprising means for limiting rotation of the wheel in the first direction.

26. A device according to claim 24, wherein the wheel includes a radially extending tooth positioned to contact a fixed member and limit rotation of the wheel in the first direction.

27. A device according to claim 24, wherein the ratchet mechanism further includes a gear secured to the lead screw coaxially within the wheel and having teeth extending radially outwardly towards the wheel, and wherein a pawl extends radially inwardly from the wheel and engages the teeth of the gears to prevent relative rotation between the wheel and the gear during rotation of the wheel in the first direction and allow relative rotation between the wheel and the gear during rotation of the wheel in the second direction.

28. A device according to claim 20, wherein the shape memory element comprises a wire.

29. A device according to claim 20, wherein the elongated shape memory element is made of a nickel and titanium alloy.

30. A device according to claim 20, wherein the side wall of the reservoir and the plunger have a non-circular cross-section.

31. A device according to claim 20, wherein the side wall of the reservoir includes a channel extending parallel with the lead screw, and the plunger includes a protrusion slidingly received in the channel.

32. A device according to claim 20, wherein:

the reservoir includes an end wall defining the outlet connected to the exit port assembly;

the threaded lead screw extends to the end wall; and the plunger is non-rotatable with respect to the side wall of the reservoir and is threadedly received on the lead screw.

33. A device according to claim 32, wherein the plunger includes an insert threadedly received on the lead screw and wherein the threaded insert and the plunger are made from different materials.

34. A device according to claim 20, further comprising:
a local processor connected to ends of the shape memory element and programmed to provide charges to the shape memory element based upon flow instructions;
a wireless receiver connected to the local processor for receiving flow instructions from a separate, remote control device and delivering the flow instructions to the local processor; and
a housing containing the reservoir, the exit port assembly, the dispenser, the local processor and the wireless receiver, wherein the housing is free of user input components for providing flow instructions to the local processor.

35. A system including a fluid delivery device according to claim 34, and further comprising a remote control device separate from the fluid delivery device and including:
a remote processor;
user interface components connected to the remote processor for allowing a user to provide flow instructions to the remote processor; and
a transmitter connected to the remote processor for transmitting the flow instructions to the receiver of the fluid delivery device.

36. A device according to claim 20, wherein the reservoir contains a therapeutic fluid.

37. A device according to claim 36, wherein the therapeutic fluid is insulin.

38. A device according to claim 20, wherein the exit port assembly includes a transcutaneous patient access tool.

39. A device according to claim 38, wherein the transcutaneous patient access tool comprises a needle.

40. A device according to claim 20, wherein an end of the shape memory element is connected to an auxiliary component of the fluid delivery device for actuating the auxiliary component upon at least a first charge applied to the shape memory element.

41. A device according to claim 40, wherein the auxiliary component comprises a spring-loaded needle of the exit port assembly and the shape memory element is arranged to release the spring-loaded needle for insertion into a patient upon first decreasing from an uncharged length to a charged length when the first charge is applied to the shape memory element.

42. A device according to claim 20, further comprising a local processor connected to ends of the shape memory element and programmed to provide charges to the shape memory element based upon flow instructions.

43. A device according to claim 42, further comprising a power supply connected to the local processor.

44. A device for delivering fluid to a patient, comprising:
an exit port assembly;
a reservoir including a side wall extending towards an outlet connected to the exit port assembly;
a threaded lead screw at least partly received in the reservoir and extending towards the outlet;
a plunger secured to the lead screw and having an outer periphery linearly slideable along the side wall of the reservoir, wherein the plunger and the lead screw are operatively arranged such that rotation of the lead screw in a first direction causes the plunger to slide along the side wall towards the outlet of the reservoir; and
a dispenser including,
a gear secured to the lead screw and including radially extending teeth positioned to contact a first fixed member and prevent rotation of the gear and the lead screw in the second direction,
a slide positioned for linear movement adjacent the gear between a second fixed member and a third fixed member, the slide including a finger for engaging the teeth of the gear, and wherein the finger and the teeth are adapted such that linear movement of the slide past the gear towards the second fixed member causes rotation of the gear in the first direction while linear movement of the slide past the gear towards the third fixed member causes no rotation of the gear,
an elongated shape memory element having a changeable length decreasing from an uncharged length to a charged length when at least one charge is applied to the shape memory element, the shape memory element connected between the slide and the third fixed member such that the changeable length of the shape memory element decreasing from an uncharged length to a charged length causes linear movement of the slide past the gear towards the third fixed member, and
an actuation element connected between the slide and the second fixed member for causing linear movement of the slide past the gear towards the second fixed member.

45. A device according to claim 44, wherein the actuation element comprises a spring.

46. A device according to claim 45, wherein the spring is a helical tension spring that expands upon the shape memory element decreasing from an uncharged length to a charged length, and contracts to increase the shape memory element from a charged length to an uncharged length.

47. A device according to claim 44, wherein the actuation element comprises a second shape memory element having a changeable length decreasing from an uncharged length to a charged length when at least one charge is applied to the shape memory element.

48. A device according to claim 44, wherein the shape memory element comprises a wire.

49. A device according to claim 44, wherein the shape memory element is made of a nickel and titanium alloy.

50. A device according to claim 44, wherein the side wall of the reservoir and the plunger have a non-circular cross-section.

51. A device according to claim 44, wherein the side wall of the reservoir includes a channel extending parallel with the lead screw, and the plunger includes a protrusion slidingly received in the channel.

52. A device according to claim 44, wherein:
the reservoir includes an end wall defining the outlet connected to the exit port assembly;
the threaded lead screw extends to the end wall; and
the plunger is non-rotatable with respect to the side wall of the reservoir and is threadedly received on the lead screw.

53. A device according to claim 52, wherein the plunger includes an insert threadedly received on the lead screw and wherein the threaded insert and the plunger are made from different materials.

54. A device according to claim 44, further comprising:
a local processor connected to ends of the shape memory element and programmed to provide charges to the shape memory element based upon flow instructions;
a wireless receiver connected to the local processor for receiving flow instructions from a separate, remote control device and delivering the flow instructions to the local processor; and a housing containing the reservoir, the exit port assembly, the dispenser, the local processor and the wireless receiver, wherein the housing is free of user input components for providing flow instructions to the local processor.

55. A system including a fluid delivery device according to claim 54, and further comprising a remote control device separate from the fluid delivery device and including:

a remote processor;

user interface components connected to the remote processor for allowing a user to provide flow instructions to the remote processor; and a transmitter connected to the remote processor for transmitting the flow instructions to the receiver of the fluid delivery device.

56. A device according to claim 44, wherein the reservoir contains a therapeutic fluid.

57. A device according to claim 56, wherein the therapeutic fluid is insulin.

58. A device according to claim 44, wherein the exit port assembly includes a transcutaneous patient access tool.

59. A device according to claim 58, wherein the transcutaneous patient access tool comprises a needle.

60. A device according to claim 44, wherein an end of the shape memory element is connected to an auxiliary component of the fluid delivery device for actuating the auxiliary component upon at least a first charge applied to the shape memory element.

61. A device according to claim 60, wherein the auxiliary component comprises a spring-loaded needle of the exit port assembly and the shape memory element is arranged to release the spring-loaded needle for insertion into a patient upon first decreasing from an uncharged length to a charged length when the first charge is applied to the shape memory element.

62. A device according to claim 44, further comprising a local processor connected to ends of the shape memory element and programmed to provide charges to the shape memory element based upon flow instructions.

63. A device according to claim 62, further comprising a power supply connected to the local processor.

64. A device for delivering fluid to a patient, comprising:

an exit port assembly;

a reservoir including a side wall extending towards an outlet connected to the exit port assembly;

a threaded lead screw received at least partly within the reservoir and extending towards the outlet;

a plunger secured to the lead screw and having an outer periphery linearly slideable along the side wall of the reservoir, wherein the plunger and the lead screw are operatively arranged such that rotation of the lead screw in a first direction causes the plunger to slide along the side wall towards the outlet of the reservoir; and a dispenser including, a gear secured to the lead screw and including radially extending teeth positioned to contact a first fixed member and prevent rotation of the gear and the lead screw in the second direction, a slide positioned for linear movement between the gear and a second fixed member, the slide including a finger for engaging the teeth of the gear, wherein the finger and the teeth are adapted such that linear movement of the slide towards the gear causes rotation of the gear in the first direction while linear movement of the slide towards the second fixed member causes no rotation of the gear, an elongated shape memory element having a changeable length decreasing from an uncharged length to a charged length when at least one charge is applied to the shape memory element, the shape memory element connected between the slide and the second fixed member such that the changeable length of the shape memory element decreasing from an uncharged length to a charged length causes linear movement of the slide towards the second fixed member, and an actuation element connected between the slide and the second fixed member for causing linear movement of the slide towards the gear.

65. A device according to claim 64, wherein the actuation element comprises a spring.

66. A device according to claim 65, wherein the spring is a helical compression spring that contracts upon the shape memory element decreasing from an uncharged length to a charged length, and expands to increase the shape memory element from a charged length to an uncharged length.

67. A device according to claim 64, wherein the shape memory element comprises a wire.

68. A device according to claim 64, wherein the shape memory element is made of a nickel and titanium alloy.

69. A device according to claim 64, wherein the side wall of the reservoir and the plunger have a non-circular cross-section.

70. A device according to claim 64, wherein the side wall of the reservoir includes a channel extending parallel with the lead screw, and the plunger includes a protrusion slidingly received in the channel.

71. A device according to claim 64, wherein:

the reservoir includes an end wall defining the outlet connected to the exit port assembly;

the threaded lead screw extends to the end wall; and the plunger is non-rotatable with respect to the side wall of the reservoir and is threadedly received on the lead screw.

72. A device according to claim 71, wherein the plunger includes an insert threadedly received on the lead screw and wherein the threaded insert and the plunger are made from different materials.

73. A device according to claim 64, further comprising:

a local processor connected to ends of the shape memory element and programmed to provide charges to the shape memory element based upon flow instructions;

a wireless receiver connected to the local processor for receiving flow instructions from a separate, remote control device and delivering the flow instructions to the local processor; and a housing containing the reservoir, the exit port assembly, the dispenser, the local processor and the wireless receiver, wherein the housing is free of user input components for providing flow instructions to the local processor.

74. A system including a fluid delivery device according to claim 73, and further comprising a remote control device separate from the fluid delivery device and including:

a remote processor;

user interface components connected to the remote processor for allowing a user to provide flow instructions to the remote processor; and a transmitter connected to the remote processor for transmitting the flow instructions to the receiver of the fluid delivery device.

75. A device according to claim 64, wherein the reservoir contains a therapeutic fluid.

76. A device according to claim 75, wherein the therapeutic fluid is insulin.

77. A device according to claim 64, wherein the exit port assembly includes a transcutaneous patient access tool.

78. A device according to claim 77, wherein the transcutaneous patient access tool comprises a needle.

79. A device according to claim 64, wherein an end of the shape memory element is connected to an auxiliary component of the fluid delivery device for actuating the auxiliary component upon at least a first charge applied to the shape memory element.

80. A device according to claim 79, wherein the auxiliary component comprises a spring-loaded needle of the exit port assembly and the shape memory element is arranged to release the spring-loaded needle for insertion into a patient upon first decreasing from an uncharged length to a charged length when the first charge is applied to the shape memory element.

81. A device according to claim 64, further comprising a local processor connected to ends of the shape memory element and programmed to provide charges to the shape memory element based upon flow instructions.

82. A device according to claim 81, further comprising a power supply connected to the local processor.

83. A device according to claim 64, wherein the dispenser further comprises:

a latch movable between the slide and a third fixed member, the latch for engaging a shoulder of the slide when the latch is moved towards the slide to prevent movement of the slide towards the gear;

a second elongated shape memory element having a changeable length decreasing from an uncharged length to a charged length when at least one charge is applied to the second shape memory element, the second shape memory element connected between the latch and the third fixed member such that the changeable length of the second shape memory element decreasing from an uncharged length to a charged length causes movement of the latch towards the third fixed member, and a second actuation element connected between the latch and the third fixed member for causing movement of the latch towards the slide.

84. A device according to claim 83, wherein the latch is linearly movable between the slide and the third fixed member.

85. A device according to claim 83, wherein the second actuation element comprises a second spring.

86. A device according to claim 85, wherein the second spring is a helical compression spring that contracts upon the second shape memory element decreasing from an uncharged length to a charged length, and expands to increase the second shape memory element from a charged length to an uncharged length.

87. A device according to claim 83, wherein the second shape memory element comprises a wire.

88. A device according to claim 83, wherein the second shape memory element is made of a nickel and titanium alloy.

89. An exit port assembly for delivering fluid to a patient comprising:

a fixed member defining a channel having an outlet;

a transcutaneous patient access tool received for sliding movement in the channel towards the outlet;

an actuation element connected between the tool and a second fixed member for causing sliding movement of the tool towards the outlet of the channel;

a movable latch positioned within the channel between the tool and the outlet; and an elongated shape memory element having a changeable length decreasing from an uncharged length to a charged length when at least one charge is applied to the shape memory element, the shape memory element connected to the latch such that the changeable length of the shape memory element decreasing from an uncharged length to a charged length causes movement of the latch out of the channel.

90. A device according to claim 89, wherein the transcutaneous patient access tool comprises a needle.

91. A device according to claim 89, wherein the actuation element comprises a spring.

92. A device according to claim 91, wherein the spring is a helical compression spring that expands to cause sliding movement of the tool towards the outlet of the channel.

93. A device according to claim 89, wherein the shape memory element comprises a wire.

94. A device according to claim 83, wherein the shape memory element is made of a nickel and titanium alloy.

95. A device for delivering fluid to a patient, comprising:

an exit port assembly;

a fill port;

a reservoir including a side wall extending towards an outlet connected to the exit port assembly and an inlet connected to the fill port;

a threaded lead screw received at least partly within the reservoir and extending towards the outlet and the inlet of the reservoir;

a plunger having an outer periphery slidably received on the side wall of the reservoir and an inner periphery slidably received on the lead screw and wherein the plunger is non-rotatable with respect to the side wall, the plunger including, an insert having a threaded surface mateable with the threaded lead screw, a spring biasing the threaded surface of the insert against the threaded lead screw such that rotating the lead screw in a first direction causes the plunger to slide along the side wall towards the outlet of the reservoir, and an elongated shape memory element having a changeable length decreasing from an uncharged length to a charged length when at least one charge is applied to the shape memory element, the shape memory element having a first end secured to the insert and a second end extending radially outwardly from the insert and secured to the plunger, such that the changeable length of the shape memory element decreasing from an uncharged length to a charged length pulls the threaded surface of the insert away from the threaded lead screw such that the plunger can slide along the lead screw and away from the inlet of the reservoir.

96. A device according to claim 95, wherein the shape memory element comprises a wire.

97. A device according to claim 95, wherein the elongated shape memory element is made of a nickel and titanium alloy.

98. A device according to claim 95, further comprising a dispenser operatively connected to the lead screw for rotating the lead screw to advance the plunger towards the outlet of the reservoir.

99. A device according to claim 98, wherein the dispenser comprises a rotary motor mated to the lead screw.

100. A device according to claim 95, wherein the side wall of the reservoir and the plunger have a non-circular cross-section.

101. A device according to claim 95, wherein the side wall of the reservoir includes a channel extending parallel with the lead screw, and the plunger includes a protrusion slidingly received in the channel.

102. A device according to claim 95, wherein the threaded lead screw is made from a plastic.

103. A device according to claim 95, wherein the plunger includes an outer layer of resiliently flexible material providing a substantially fluid-tight interface between the outer periphery of the plunger and the side wall of the reservoir and the inner periphery of the plunger and the lead screw.

104. A device according to claim 95, wherein the reservoir contains a therapeutic fluid.

105. A device according to claim 104, wherein the therapeutic fluid is insulin.

106. A device according to claim 95, wherein the exit port assembly includes a transcutaneous patient access tool.

107. A device according to claim 106, wherein the transcutaneous patient access tool comprises a needle.

108. A device according to claim 95, further comprising a power supply connected to the ends of the shape memory element.

109. A device according to claim 95, further comprising a needle pierceable septum contained in the fill port.

110. A device according to claim 95, further comprising a sensor adapted and arranged to provide a signal upon the presence of a needle in the fill port.

111. A device according to claim 110, further comprising a local processor connected to the ends of the shape memory element and connected to the fill port sensor and programmed to provide a charge to the shape memory element upon receiving a signal from the fill port sensor.

112. A device according to claim 111, further comprising a power supply connected to the local processor.

113. A device for delivering fluid to a patient, comprising:
an exit port assembly;
a fill port;
a reservoir including a side wall extending towards an outlet connected to the exit port assembly and an inlet connected to the fill port;
a threaded lead screw received at least partly within the reservoir and extending towards the outlet and the inlet of the reservoir;
a linearly fixed annular gear coaxially positioned on the threaded lead screw adjacent the reservoir and including,
an insert having a threaded surface mateable with the threaded lead screw,
a spring biasing the threaded surface of the insert against the threaded lead screw such that rotating the gear in a first direction causes the lead screw to move linearly towards the outlet of the reservoir, and
an elongated shape memory element having a changeable length decreasing from an uncharged length to a charged length when at least one charge is applied to the shape memory element, the shape memory element having a first end secured to the insert and a second end extending radially outwardly from the insert and secured to the gear, such that the changeable length of the shape memory element decreasing from an uncharged length to a charged length pulls the threaded surface of the insert away from the threaded lead screw such that the lead screw is movable linearly through the gear and away from the inlet of the reservoir; and
a plunger secured to the lead screw and having an outer periphery linearly slideable along the side wall of the reservoir.

114. A device according to claim 113, wherein the shape memory element comprises a wire.

115. A device according to claim 113, wherein the elongated shape memory element is made of a nickel and titanium alloy.

116. A device according to claim 113, further comprising a dispenser operatively arranged to rotate the gear in the first direction.

117. A device according to claim 116, wherein the dispenser includes at least one shape memory element.

118. A device according to claim 113, wherein the plunger is non-rotatable with respect to the side wall of the reservoir.

119. A device according to claim 118, wherein the side wall of the reservoir and the plunger have a non-circular cross-section.

120. A device according to claim 119, wherein the side wall of the reservoir includes a channel extending parallel with the lead screw, and the plunger includes a protrusion slidingly received in the channel.

121. A device according to claim 113, wherein the reservoir contains a therapeutic fluid.

122. A device according to claim 121, wherein the therapeutic fluid is insulin.

123. A device according to claim 113, wherein the exit port assembly includes a transcutaneous patient access tool.

124. A device according to claim 123, wherein the transcutaneous patient access tool comprises a needle.

125. A device according to claim 113, further comprising a power supply connected to the ends of the shape memory element.

126. A device according to claim 113, further comprising a needle pierceable septum contained in the fill port.

127. A device according to claim 113, further comprising a sensor adapted and arranged to provide a signal upon the presence of a needle in the fill port.

128. A device according to claim 127, further comprising a local processor connected to the ends of the shape memory element and connected to the fill port sensor and programmed to provide a charge to the shape memory element upon receiving a signal from the fill port sensor.

129. A device according to claim 128, further comprising a power supply connected to the local processor.

* * * * *